US008512288B2

(12) United States Patent
Moberg et al.

(10) Patent No.: US 8,512,288 B2
(45) Date of Patent: Aug. 20, 2013

(54) INFUSION MEDIUM DELIVERY DEVICE AND METHOD WITH DRIVE DEVICE FOR DRIVING PLUNGER IN RESERVOIR

(75) Inventors: Sheldon B. Moberg, Thousand Oaks, CA (US); Ian B. Hanson, Northridge, CA (US); Paul F. Bente, IV, Los Angeles, CA (US); Ruth Marie Tieck, Los Angeles, CA (US); Julian D. Kavazov, Arcadia, CA (US); Christopher G. Griffin, Sylmar, CA (US); Colin A. Chong, Burbank, CA (US); Mark D. Holt, Moorpark, CA (US); R. Paul Mounce, Burbank, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 1029 days.

(21) Appl. No.: 11/515,225

(22) Filed: Sep. 1, 2006

(65) Prior Publication Data

US 2008/0051727 A1 Feb. 28, 2008

Related U.S. Application Data

(60) Provisional application No. 60/839,822, filed on Aug. 23, 2006.

(51) Int. Cl.
*A61M 1/00* (2006.01)
*A61M 5/00* (2006.01)

(52) U.S. Cl.
USPC .......................................... 604/152; 604/232

(58) Field of Classification Search
USPC ................. 604/232–235, 151, 152, 154, 155, 604/150
See application file for complete search history.

(56) References Cited

U.S. PATENT DOCUMENTS

| 2,570,625 | A | | 10/1951 | Zimmerman et al. |
| 2,644,450 | A | | 7/1953 | J.E. Krewson |
| 3,623,474 | A | * | 11/1971 | Heilman et al. ............... 604/155 |

(Continued)

FOREIGN PATENT DOCUMENTS

| DE | 10 2004 055 870 A1 | 11/2004 |
| DE | 1020040 55 870 A1 | 5/2006 |

(Continued)

OTHER PUBLICATIONS

Partial International Search Report dated Jan. 2, 2008 for PCT application PCT/US2007/076474.

(Continued)

*Primary Examiner* — Kevin C Sirmons
*Assistant Examiner* — Andrew Gilbert
(74) *Attorney, Agent, or Firm* — Foley & Lardner LLP

(57) ABSTRACT

A delivery device includes a durable housing portion and a separable disposable portion that selectively engage and disengage from each other. The disposable housing portion secures to the patient-user and may be disposed of after it has been in use for a prescribed period. Components that normally come into contact with a patient-user or with infusion medium are supported by the disposable housing portion, while the durable housing portion supports other components such as electronics and a drive device. A reservoir is supported by the disposable housing portion and has a moveable plunger that operatively couples to the drive device, when the disposable and durable housing portions are engaged.

34 Claims, 13 Drawing Sheets

(56) References Cited

U.S. PATENT DOCUMENTS

| | | | |
|---|---|---|---|
| 3,662,753 A | 5/1972 | Tassell | |
| 3,802,430 A | 4/1974 | Schwebel et al. | |
| 3,963,151 A | 6/1976 | North, Jr. | |
| 4,064,879 A | 12/1977 | Leibinsohn | |
| 4,089,624 A | 5/1978 | Nichols et al. | |
| 4,117,841 A | 10/1978 | Perrotta et al. | |
| 4,215,701 A | 8/1980 | Raitto | |
| 4,373,535 A | 2/1983 | Martell | |
| 4,448,206 A | 5/1984 | Martell | |
| 4,493,704 A | 1/1985 | Beard et al. | |
| 4,508,532 A | 4/1985 | Drews et al. | |
| 4,585,435 A | 4/1986 | Vaillancourt | |
| 4,684,366 A | 8/1987 | Denny et al. | |
| 4,838,857 A | 6/1989 | Strowe et al. | |
| 4,883,101 A | 11/1989 | Strong | |
| 4,913,703 A | 4/1990 | Pasqualucci et al. | |
| 4,976,696 A | 12/1990 | Sanderson et al. | |
| 4,986,820 A | 1/1991 | Fischer | |
| 4,994,034 A | 2/1991 | Biotich et al. | |
| 5,002,527 A | 3/1991 | Reller et al. | |
| 5,053,001 A | 10/1991 | Reller et al. | |
| 5,062,834 A | 11/1991 | Gross et al. | |
| 5,090,963 A | 2/1992 | Gross et al. | |
| 5,156,591 A | 10/1992 | Gross et al. | |
| 5,176,502 A | 1/1993 | Sanderson et al. | |
| 5,186,805 A | 2/1993 | Gross et al. | |
| 5,190,522 A | 3/1993 | Wojcicki et al. | |
| 5,203,506 A | 4/1993 | Gross et al. | |
| 5,232,449 A | 8/1993 | Stern et al. | |
| 5,242,406 A | 9/1993 | Gross et al. | |
| 5,242,408 A | 9/1993 | Jhuboo et al. | |
| 5,246,147 A | 9/1993 | Gross et al. | |
| 5,254,096 A | 10/1993 | Rondelet et al. | |
| 5,259,732 A | 11/1993 | Stern | |
| 5,261,884 A | 11/1993 | Stern et al. | |
| 5,275,582 A | 1/1994 | Wimmer | |
| 5,295,966 A | 3/1994 | Stern et al. | |
| 5,295,967 A | 3/1994 | Rondelet et al. | |
| 5,312,364 A | 5/1994 | Jacobs | |
| 5,356,632 A | 10/1994 | Gross et al. | |
| 5,367,891 A | 11/1994 | Furuyama | |
| 5,385,559 A | 1/1995 | Mannix | |
| 5,409,236 A | 4/1995 | Therrien | |
| 5,425,706 A | 6/1995 | Gross et al. | |
| 5,496,285 A | 3/1996 | Schumacher et al. | |
| 5,527,288 A | 6/1996 | Gross et al. | |
| 5,697,916 A | 12/1997 | Schraga | |
| 5,704,520 A | 1/1998 | Gross | |
| 5,800,420 A | 9/1998 | Gross et al. | |
| 5,807,375 A | 9/1998 | Gross et al. | |
| 5,820,622 A | 10/1998 | Gross et al. | |
| 5,848,991 A | 12/1998 | Gross et al. | |
| 5,851,549 A | 12/1998 | Svec | |
| 5,858,001 A | 1/1999 | Tsals et al. | |
| 5,865,803 A | 2/1999 | Major | |
| 5,871,125 A | 2/1999 | Gross | |
| 5,933,287 A | 8/1999 | Muller | |
| 5,951,523 A | 9/1999 | Osterlind et al. | |
| 5,954,697 A * | 9/1999 | Srisathapat et al. | 604/155 |
| 5,957,889 A | 9/1999 | Poulsen et al. | |
| 5,984,894 A | 11/1999 | Poulsen et al. | |
| 5,997,501 A | 12/1999 | Gross et al. | |
| 6,003,736 A | 12/1999 | Ljunggren | |
| 6,033,377 A | 3/2000 | Rasmussen et al. | |
| 6,042,565 A * | 3/2000 | Hirschman et al. | 604/155 |
| 6,099,504 A | 8/2000 | Gross et al. | |
| 6,126,643 A | 10/2000 | Vaillancouert | |
| 6,186,982 B1 | 2/2001 | Gross et al. | |
| 6,229,584 B1 | 5/2001 | Chuo et al. | |
| 6,248,093 B1 * | 6/2001 | Moberg | 604/131 |
| 6,261,272 B1 | 7/2001 | Gross et al. | |
| 6,275,717 B1 | 8/2001 | Gross et al. | |
| 6,277,095 B1 | 8/2001 | Kriesel et al. | |
| 6,312,409 B1 | 11/2001 | Gross | |
| 6,314,317 B1 | 11/2001 | Willis | |
| 6,346,095 B1 | 2/2002 | Gross et al. | |
| 6,364,865 B1 | 4/2002 | Lavi et al. | |
| 6,406,455 B1 | 6/2002 | Willis et al. | |
| 6,423,035 B1 * | 7/2002 | Das et al. | 604/155 |
| 6,440,096 B1 | 8/2002 | Lastovich et al. | |
| 6,461,329 B1 * | 10/2002 | Van Antwerp et al. | 604/111 |
| 6,474,219 B2 | 11/2002 | Klitmose et al. | |
| 6,478,771 B1 | 11/2002 | Lavi et al. | |
| 6,485,461 B1 | 11/2002 | Mason et al. | |
| 6,485,465 B2 * | 11/2002 | Moberg et al. | 604/154 |
| 6,490,483 B2 | 12/2002 | Willis | |
| 6,503,225 B1 | 1/2003 | Kirsch et al. | |
| 6,508,788 B2 | 1/2003 | Preuthun | |
| 6,537,251 B2 | 3/2003 | Klitmose | |
| 6,585,707 B2 | 7/2003 | Cabiri et al. | |
| 6,589,229 B1 | 7/2003 | Connelly et al. | |
| 6,595,956 B1 * | 7/2003 | Gross et al. | 604/141 |
| 6,607,509 B2 | 8/2003 | Bobroff et al. | |
| 6,607,513 B1 | 8/2003 | Down et al. | |
| 6,613,019 B2 | 9/2003 | Munk | |
| 6,616,627 B2 | 9/2003 | Willis et al. | |
| 6,626,874 B1 | 9/2003 | Duchamp | |
| 6,641,565 B1 | 11/2003 | Lavi et al. | |
| 6,641,566 B2 * | 11/2003 | Douglas et al. | 604/155 |
| 6,645,181 B1 | 11/2003 | Lavi et al. | |
| 6,656,147 B1 | 12/2003 | Wilkinson et al. | |
| 6,656,158 B2 | 12/2003 | Mahoney et al. | |
| 6,656,159 B2 * | 12/2003 | Flaherty | 604/151 |
| 6,669,669 B2 | 12/2003 | Flaherty et al. | |
| 6,689,100 B2 | 2/2004 | Connelly et al. | |
| 6,692,457 B2 | 2/2004 | Flaherty | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |
| 6,716,195 B2 | 4/2004 | Nolan, Jr. et al. | |
| 6,723,068 B2 | 4/2004 | Lavi et al. | |
| 6,723,072 B2 | 4/2004 | Flaherty et al. | |
| 6,740,059 B2 | 5/2004 | Flaherty | |
| 6,749,587 B2 * | 6/2004 | Flaherty | 604/151 |
| 6,767,188 B2 | 7/2004 | Vrane et al. | |
| 6,768,425 B2 | 7/2004 | Flaherty et al. | |
| 6,786,246 B2 | 9/2004 | Ohms et al. | |
| 6,808,506 B2 | 10/2004 | Lastovich et al. | |
| 6,830,558 B2 | 12/2004 | Flaherty et al. | |
| 6,830,560 B1 | 12/2004 | Gross et al. | |
| 6,886,724 B2 | 5/2005 | Hung | |
| 6,899,699 B2 | 5/2005 | Enggaard | |
| 6,936,006 B2 | 8/2005 | Sabra | |
| 6,939,324 B2 | 9/2005 | Gonnelli et al. | |
| 6,948,918 B2 | 9/2005 | Hansen | |
| 6,952,604 B2 | 10/2005 | DeNuzzio et al. | |
| 6,960,184 B2 | 11/2005 | Willis et al. | |
| 6,960,192 B1 | 11/2005 | Flaherty et al. | |
| 6,997,911 B2 | 2/2006 | Klitmose | |
| 7,008,399 B2 | 3/2006 | Larsen et al. | |
| 7,018,360 B2 | 3/2006 | Flaherty et al. | |
| 7,027,478 B2 | 4/2006 | Ackley | |
| 7,029,455 B2 | 4/2006 | Flaherty | |
| 7,083,592 B2 | 8/2006 | Lastovich et al. | |
| 7,083,599 B2 | 8/2006 | Alchas et al. | |
| 7,115,108 B2 | 10/2006 | Wilkinson et al. | |
| 7,128,727 B2 | 10/2006 | Flaherty et al. | |
| 7,133,329 B2 | 11/2006 | Skyggebjerg et al. | |
| 7,137,964 B2 | 11/2006 | Flaherty | |
| 7,144,384 B2 | 12/2006 | Gorman et al. | |
| 7,150,409 B2 | 12/2006 | Gonnelli et al. | |
| 7,156,838 B2 | 1/2007 | Gabel et al. | |
| 7,187,969 B2 | 3/2007 | Willis | |
| 7,220,889 B2 | 5/2007 | Sigurjonsson et al. | |
| 7,306,578 B2 | 12/2007 | Gray et al. | |
| 7,318,816 B2 | 1/2008 | Bobroff et al. | |
| 7,338,472 B2 * | 3/2008 | Shearn | 604/155 |
| 7,361,156 B2 | 4/2008 | Joyce et al. | |
| 7,708,717 B2 | 5/2010 | Estes et al. | |
| 7,744,589 B2 | 6/2010 | Mounce et al. | |
| 7,955,305 B2 | 6/2011 | Moberg et al. | |
| 8,409,143 B2 * | 4/2013 | Lanigan et al. | 604/152 |
| 2001/0041869 A1 | 11/2001 | Causey et al. | |
| 2002/0040208 A1 | 4/2002 | Flaherty et al. | |

| | | | |
|---|---|---|---|
| 2002/0072733 A1 | 6/2002 | Flaherty | |
| 2002/0123740 A1 | 9/2002 | Flaherty et al. | |
| 2002/0126036 A1 | 9/2002 | Flaherty et al. | |
| 2002/0169439 A1 | 11/2002 | Flaherty | |
| 2003/0055380 A1 | 3/2003 | Flaherty | |
| 2003/0073952 A1 | 4/2003 | Flaherty et al. | |
| 2003/0097092 A1 | 5/2003 | Flaherty | |
| 2003/0125672 A1 | 7/2003 | Adair et al. | |
| 2003/0167035 A1 | 9/2003 | Flaherty et al. | |
| 2003/0167036 A1 | 9/2003 | Flaherty | |
| 2003/0199824 A1 | 10/2003 | Mahoney et al. | |
| 2003/0199825 A1 | 10/2003 | Flaherty | |
| 2003/0212364 A1 | 11/2003 | Mann et al. | |
| 2003/0229310 A1 | 12/2003 | Flaherty et al. | |
| 2003/0233069 A1 | 12/2003 | Gillespie, Jr. et al. | |
| 2004/0002682 A1 | 1/2004 | Kovelman et al. | |
| 2004/0010207 A1 | 1/2004 | Flaherty et al. | |
| 2004/0011866 A1 | 1/2004 | Saad | |
| 2004/0015131 A1 | 1/2004 | Flaherty et al. | |
| 2004/0064088 A1 | 4/2004 | Gorman et al. | |
| 2004/0064096 A1 | 4/2004 | Flaherty et al. | |
| 2004/0073095 A1 | 4/2004 | Causey et al. | |
| 2004/0078028 A1 | 4/2004 | Flaherty et al. | |
| 2004/0087894 A1 | 5/2004 | Flaherty | |
| 2004/0092865 A1 | 5/2004 | Flaherty et al. | |
| 2004/0116866 A1 | 6/2004 | Gorman et al. | |
| 2004/0158207 A1 | 8/2004 | Hunn et al. | |
| 2004/0199140 A1 | 10/2004 | Rue et al. | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0022274 A1 | 1/2005 | Campbell et al. | |
| 2005/0065760 A1 | 3/2005 | Murtfeldt et al. | |
| 2005/0119618 A1 | 6/2005 | Gonnelli | |
| 2005/0137530 A1 | 6/2005 | Campbell et al. | |
| 2006/0184119 A1 | 8/2006 | Remde et al. | |
| 2006/0253085 A1 | 11/2006 | Geismar et al. | |
| 2006/0264835 A1 | 11/2006 | Nielsen et al. | |
| 2006/0264894 A1* | 11/2006 | Moberg et al. ............... 604/503 | |
| 2007/0073235 A1* | 3/2007 | Estes et al. .................. 604/151 | |
| 2007/0293826 A1 | 12/2007 | Wall et al. | |
| 2008/0051710 A1 | 2/2008 | Moberg et al. | |
| 2008/0051730 A1 | 2/2008 | Bikovsky | |
| 2008/0269682 A1 | 10/2008 | Kavazov et al. | |
| 2008/0269687 A1 | 10/2008 | Chong et al. | |
| 2011/0160654 A1 | 6/2011 | Hanson et al. | |
| 2012/0004602 A1 | 1/2012 | Hanson et al. | |

FOREIGN PATENT DOCUMENTS

| | | | |
|---|---|---|---|
| DE | 20 2007 006 3 | 8/2007 | |
| EP | 1 462 134 A1 | 9/2004 | |
| EP | 1 527 792 A1 | 5/2005 | |
| EP | 1 347 705 | 12/2005 | |
| EP | 1 423 079 | 7/2006 | |
| EP | 1 135 056 | 8/2006 | |
| EP | 1 702 635 | 9/2006 | |
| EP | 1 545 657 | 11/2006 | |
| EP | 1 546 556 | 12/2006 | |
| EP | 1 341 569 | 1/2007 | |
| EP | 1 461 070 | 1/2007 | |
| EP | 1 464 351 | 1/2007 | |
| EP | 1 309 366 | 2/2007 | |
| EP | 0 944 648 | 3/2007 | |
| EP | 1 646 412 | 3/2007 | |
| EP | 1 095 668 | 4/2007 | |
| FR | 1496026 | 9/1967 | |
| GB | 1 452 104 | 10/1976 | |
| GB | 2 176 711 A | 1/1987 | |
| GB | 2 176 711 A0 | 1/1987 | |
| GB | 2 207 652 A | 2/1989 | |
| GB | 2 207 652 A0 | 2/1989 | |
| WO | WO-95/23015-0 | 11/1995 | |
| WO | WO 95/32015 | 11/1995 | |
| WO | WO-95/32015 | 11/1995 | |
| WO | WO-96/26702 | 9/1996 | |
| WO | WO 96/26702 | 9/1996 | |
| WO | WO-97/44078 | 11/1997 | |
| WO | WO-97/46203-0 | 12/1997 | |
| WO | WO-99/48546 | 9/1999 | |
| WO | WO 99/59665 | 11/1999 | |
| WO | WO 00/47254 | 8/2000 | |
| WO | WO-00/69488 | 11/2000 | |
| WO | WO-01/70307 A1 | 9/2001 | |
| WO | WO 01/76684 A1 | 10/2001 | |
| WO | WO-02/02165 A2 | 1/2002 | |
| WO | WO 02/20073 A2 | 3/2002 | |
| WO | WO 02/28454 A2 | 4/2002 | |
| WO | WO 02/40083 A2 | 5/2002 | |
| WO | WO 02/49509 A2 | 6/2002 | |
| WO | WO 02/068015 A2 | 9/2002 | |
| WO | WO 03/06090 A1 | 1/2003 | |
| WO | WO 03/024504 A2 | 3/2003 | |
| WO | WO-03/026728 A1 | 4/2003 | |
| WO | WO 03/033051 A1 | 4/2003 | |
| WO | WO 03/059372 A2 | 7/2003 | |
| WO | WO 03/059372 A3 | 7/2003 | |
| WO | WO-03/072172 A2 | 9/2003 | |
| WO | WO 03/074121 A1 | 9/2003 | |
| WO | WO 03/090509 A2 | 11/2003 | |
| WO | WO 03/090819 A2 | 11/2003 | |
| WO | WO 03/090838 A1 | 11/2003 | |
| WO | WO 03/103758 A1 | 12/2003 | |
| WO | WO 03/103763 A1 | 12/2003 | |
| WO | WO 2004/006981 A2 | 1/2004 | |
| WO | WO 2004/006982 A2 | 1/2004 | |
| WO | WO 2004/030716 A2 | 4/2004 | |
| WO | WO 2004/030717 A2 | 4/2004 | |
| WO | WO 2004/047641 A2 | 6/2004 | |
| WO | WO 2004/060436 A2 | 7/2004 | |
| WO | WO 2004/093648 A2 | 11/2004 | |
| WO | WO 2004/098390 A2 | 11/2004 | |
| WO | WO 2004/098454 A2 | 11/2004 | |
| WO | WO-2004/098683 A1 | 11/2004 | |
| WO | WO 2004/110526 A1 | 12/2004 | |
| WO | WO-2005/000382 A2 | 1/2005 | |
| WO | WO-2005/072795 A2 | 8/2005 | |
| WO | WO 2005/094920 A1 | 10/2005 | |
| WO | WO-2005/097237 A1 | 10/2005 | |
| WO | WO 2006/015922 A1 | 2/2006 | |
| WO | WO 2006/018425 A2 | 2/2006 | |
| WO | WO 2006/018425 A3 | 2/2006 | |
| WO | WO 2006/018447 A2 | 2/2006 | |
| WO | WO 2006/018447 A3 | 2/2006 | |
| WO | WO 2006/024671 A1 | 3/2006 | |
| WO | WO 2006/024672 A1 | 3/2006 | |
| WO | WO 2006/032692 A1 | 3/2006 | |
| WO | WO 2006/042811 A2 | 4/2006 | |
| WO | WO 2006/042811 A3 | 4/2006 | |
| WO | WO-2006/058435 A2 | 6/2006 | |
| WO | WO 2006/072416 A2 | 7/2006 | |
| WO | WO 2006/075016 A1 | 7/2006 | |
| WO | WO 2006/077262 A1 | 7/2006 | |
| WO | WO 2006/077263 A1 | 7/2006 | |
| WO | WO 2006/084464 A1 | 8/2006 | |
| WO | WO 2006/086980 A1 | 8/2006 | |
| WO | WO 2006/089547 A1 | 8/2006 | |
| WO | WO 2006/089548 A1 | 8/2006 | |
| WO | WO 2006/089965 A1 | 8/2006 | |
| WO | WO 2006/096746 A1 | 9/2006 | |
| WO | WO 2006/097453 A1 | 9/2006 | |
| WO | WO 2006/104806 A2 | 10/2006 | |
| WO | WO 2006/108775 A2 | 10/2006 | |
| WO | WO 2006/108809 A1 | 10/2006 | |
| WO | WO 2006/116997 A1 | 11/2006 | |
| WO | WO 2006/120253 A1 | 11/2006 | |
| WO | WO 2006/125692 A1 | 11/2006 | |
| WO | WO 2007/000425 A2 | 1/2007 | |
| WO | WO 2007/000426 A2 | 1/2007 | |
| WO | WO 2007/000427 A1 | 1/2007 | |
| WO | WO 2007/038091 A2 | 4/2007 | |
| WO | WO 2007/062068 | 5/2007 | |
| WO | WO-2007/062068 A2 | 5/2007 | |
| WO | WO 2007/071255 A1 | 6/2007 | |
| WO | WO-2007/076641 | 7/2007 | |
| WO | WO 2007/087808 A1 | 8/2007 | |
| WO | WO 2007/130809 A2 | 11/2007 | |
| WO | WO-2007/130809 A2 | 11/2007 | |

| WO | WO-2008/024614 A2 | 2/2008 |
| WO | WO-2008/093063 A2 | 8/2008 |
| WO | WO 2008/093063 A2 | 8/2008 |
| WO | WO-2008/136845 | 11/2008 |
| WO | WO-2008/151241 A2 | 12/2008 |

OTHER PUBLICATIONS

International Search Report dated Feb. 29, 2008 for PCT application PCT/US2007/076474.
Partial PCT Search Report dated Mar. 5, 2009 from related PCT application No. PCT/US2008/082187.
Non-Final Office Action dated Jan. 29, 2009 for related U.S. Appl. No. 11/604,172.
Final Office Action dated Apr. 13, 2009 for related U.S. Appl. No. 11/604,171.
PCT Search Report dated Apr. 28, 2009 from related PCT application No. PCT/US2008/082186.
US-97/046203, Dec. 11, 1997, Applied Research Systems ARS Holdikngs N.V.
Final Office Action dated Jun. 17, 2009 from related U.S. Appl. No. 11/604,172.
Notice of Allowance dated Jun. 23, 2009 from related U.A. Appl. No. 11/759,725.
Office Action Dated Apr. 10, 2009 for related U.S. Appl. No. 11/588,832.
Office Action dated Apr. 13, 2009 from related U.S. Appl. No. 11/604,171.
Office Action dated Jan. 29, 2009 from related U.S. Appl. No. 11/604,172.
Office Action dated Nov. 21, 2008 from related U.S. Appl. No. 11/588,832.
Office Action dated Nov. 21, 2008 from related U.S. Appl. No. 11/604,171.
Office Action Dated Nov. 24, 2008 from related U.S. Appl. No. 11/759,725.
Office Action dated Oct. 9, 2009 from related U.S. Appl. No. 11/604,171.
Notice of Allowance dated Jan. 19, 2010 from related U.S. Appl. No. 11/759,725.
Office Action dated Feb. 17, 2010 from related U.S. Appl. No. 11/604,172.
Office Action dated Mar. 17, 2010 from related U.S. Appl. No. 11/604,171.
Office Action dated Mar. 2, 2010 from related U.S. Appl. No. 11/588,832.
Search Report dated Jan. 11, 2010 from related European patent application No. 07841183.2.
US Notice of Allowance dated Jan. 26, 2011 from related U.S. Appl. No. 11/588,832.
Notice of Allowance dated Apr. 26, 2010 from related U.S. Appl. No. 11/604,171.
Notice of Allowance dated May 14, 2010 from related U.S. Appl. No. 11/759,725.
Office Action dated May 28, 2010 from related U.S. Appl. No. 11/604,172.
Office Action dated Jan. 14, 2010 from related U.S. Appl. No. 12/411,247.
US Office Action dated Aug. 10, 2010 from related U.S. Appl. No. 11/588,832.
U.S. Notice of Allowance dated Mar. 21, 2013 from related U.S. Appl. No. 12/247,945.
U.S. Non-Final Office Action dated Nov. 26, 2012 from related U.S. Appl. No. 12/247,945.
U.S. Non-Final Office Action dated Oct. 10, 2012 from related U.S. Appl. No. 12/497,345.
U.S. Notice of Allowance dated Apr. 29, 2013 from related U.S. Appl. No. 12/497,345.

* cited by examiner

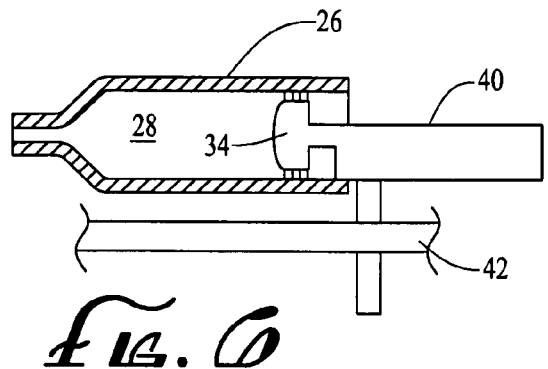
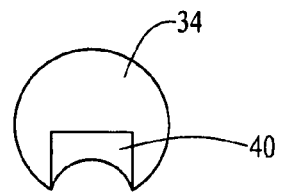
FIG. 6
FIG. 6A
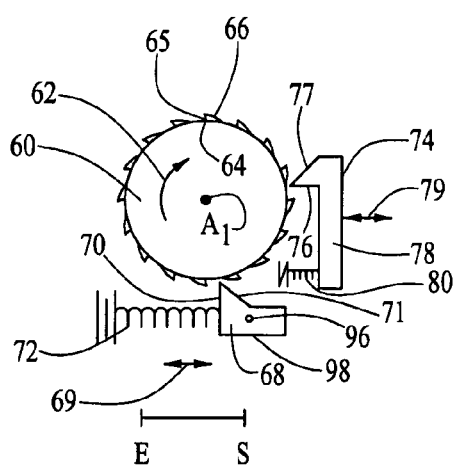
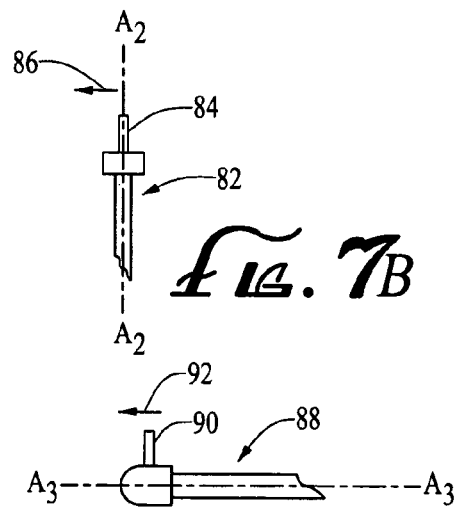
FIG. 7B
FIG. 7C
FIG. 7A
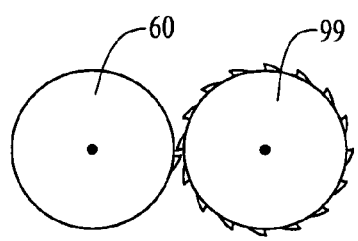
FIG. 7D

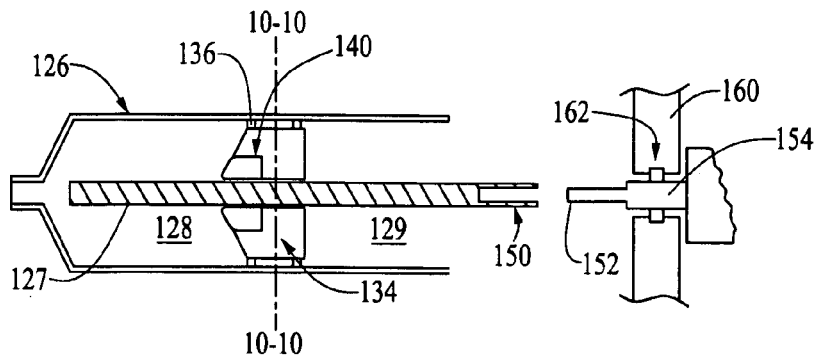
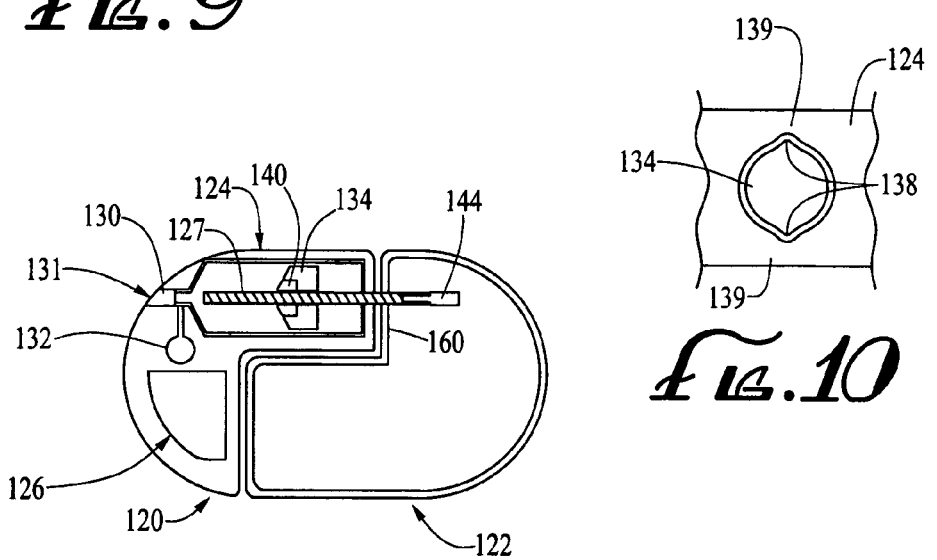
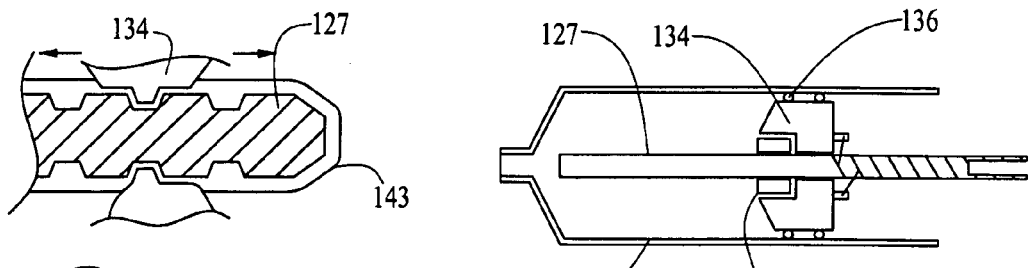

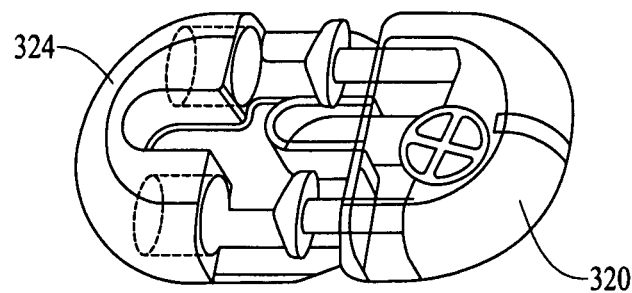
fig.16
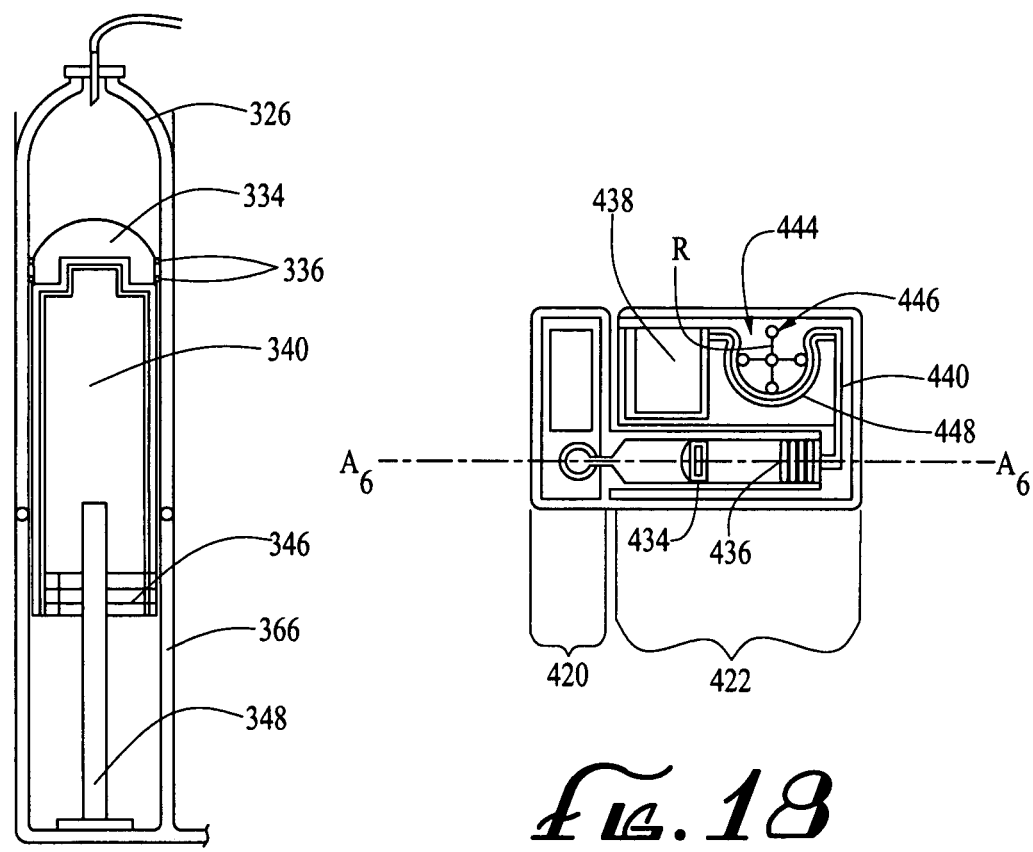
fig.17
fig.18

INFUSION MEDIUM DELIVERY DEVICE AND METHOD WITH DRIVE DEVICE FOR DRIVING PLUNGER IN RESERVOIR

The present invention relates to U.S. Provisional Patent Application 60/678,290, filed May 6, 2005 and U.S. Patent Application No. 11/211,095, filed Aug. 23, 2005, now U.S. Pat. No. 7,686,787, each of which is incorporated herein by reference in its entirety. The present invention also relates application Ser. No. 60/839,821 titled SYSTEMS AND METHODS ALLOWING FOR RESERVOIR FILLING AND INFUSION MEDIUM DELIVERY, filed Aug. 23, 2006, application no. 60/839,832, titled INFUSION MEDIUM DELIVERY.DEVICE AND METHOD WITH COMPRESSIBLE OR CURVED RESERVOIR OR CONDUIT, filed Aug. 23, 2006, application no. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, and application no. 60/839,741, titled INFUSION PUMPS AND METHODS AND DELIVERY DEVICES AND METHODS WITH SAME, filed Aug. 23, 2006. This application claims priority from Provisional Application US Application 60/839,822, filed Aug. 23, 2006, incorporated herein by reference in its entirety.

FIELD OF THE INVENTION

Embodiments of the present invention relate to an infusion medium delivery device for delivering an infusion medium to a patient-user, where the delivery device includes a base portion and a durable portion connectable to the base portion, where the base portion is securable to a patient-user's skin and can be removed and disposed of after a specified number of uses.

BACKGROUND OF THE INVENTION

Certain chronic diseases may be treated, according to modern medical techniques, by delivering a medication or other substance to a patient's body, either in a continuous manner or at particular times or time intervals within an overall time period. For example, diabetes is a chronic disease that is commonly treated by delivering defined amounts of insulin to the patient at appropriate times. Some common modes of providing an insulin therapy to a patient include delivery of insulin through manually operated syringes and insulin pens. However, other modern systems employ programmable pumps to deliver controlled amounts of insulin to a patient.

Pump type delivery devices have been configured in external devices (that connect to a patient) or implantable devices (to be implanted inside of a patient's body). External pump type delivery devices include devices designed for use in a stationary location (for example, in a hospital or clinic), and further devices configured for ambulatory or portable use (to be carried by a patient). Examples of some external pump type delivery devices are described in Published PCT Application WO 01/70307 (PCT/US01/09139) titled "Exchangeable Electronic Cards For Infusion Devices" (which is owned by the assignee of the present invention), Published PCT Application WO 04/030716 (PCT/US2003/028769) titled "Components And Methods For Patient Infusion Device," Published PCT Application WO 04/030717 (PCT/US2003/029019) titled "Dispenser Components And Methods For Infusion Device," U.S. Patent Application Publication No. 2005/0065760 titled "Method For Advising Patients Concerning Doses Of Insulin," and U.S. Pat. No. 6,589,229 titled "Wearable Self-Contained Drug Infusion Device," each of which is incorporated herein by reference in its entirety.

External pump type delivery devices may be connected in fluid-flow communication to a patient-user, for example, through a suitable hollow tubing. The hollow tubing may be connected to a hollow needle designed to pierce the patient-user's skin and deliver an infusion medium there-through. Alternatively, the hollow tubing may be connected directly to the patient-user as or through a cannula or set of micro-needles.

In contexts in which the hollow tubing is connected to the patient-user through a hollow needle that pierces the patient-user's skin, a manual insertion of the needle into the patient-user can be somewhat traumatic to the patient-user. Accordingly, insertion tools have been made to assist the insertion of a needle into the patient-user, whereby a needle is forced by a spring to quickly move from a retracted position into an extended position. One example of such an insertion tool is described in U.S. Patent Application Publication No. 2002/0022855, titled "Insertion Device For An Insertion Set And Method Of Using The Same" (assigned to the assignee of the present invention), which is incorporated herein by reference in its entirety. As the needle is moved into the extended position, the needle is quickly forced through the patient-user's skin in a single, relatively abrupt motion that can be less traumatic to a patient-user as compared to a slower, manual insertion of a needle.

As compared to syringes and insulin pens, pump type delivery devices can be significantly more convenient to a patient-user, in that accurate doses of insulin may be calculated and delivered automatically to a patient-user at any time during the day or night. Furthermore, when used in conjunction with glucose sensors or monitors, insulin pumps may be automatically controlled to provide appropriate doses of infusion medium at appropriate times of need, based on sensed or monitored levels of blood glucose.

Pump type delivery devices have become an important aspect of modern medical treatments of various types of medical conditions, such as diabetes. As pump technologies improve and doctors and patient-users become more familiar with such devices, the popularity of external medical infusion pump treatment increases and is expected to increase substantially over the next decade.

BRIEF DESCRIPTION OF THE DRAWINGS

FIG. 6 is a schematic, cross-sectional view of a portion of a reservoir and a portion of a lead shaft according to another embodiment of the invention.

FIG. 6a is a further view of the piston shaft of FIG. 6, along the longitudinal axis of the piston shaft.

FIGS. 7a-d show schematic views of escapement wheel arrangements and components thereof, for providing a controlled rotational motion.

FIG. 8 shows a schematic view of a delivery device according to a further embodiment of the present invention.

FIG. 9 shows a schematic, cross-sectional view of a reservoir and moveable plunger head of the delivery device of FIG. 8.

FIG. 10 shows a cross-sectional view taken along line 10-10 of FIG. 9.

FIGS. 11 and 12 show schematic views of embodiments of seal arrangements for the plunger head within the reservoir of FIGS. 8 and 9.

FIG. 16 shows a perspective view of a delivery device containing two reservoirs that may employ a drive device according to FIGS. 14, 15 or 17 or other suitable drive device.

FIG. 17 shows a schematic cross-sectional view of a reservoir and drive device for a delivery device according to a further embodiment of the present invention.

FIG. 18 shows a schematic view of a delivery device according to a further embodiment of the present invention.

DETAILED DESCRIPTION

The present invention relates, generally, to delivery devices, systems and methods for delivering an infusion medium, such as a drug, to a recipient, such as a medical patient-user. In particular embodiments, a delivery device includes a disposable portion that secures to the recipient and that may be readily disposed of after it has been in use for a period of time. Such embodiments may be configured to provide a reliable, user-friendly mechanism to secure the delivery device to a patient-user for delivery of a fluidic infusion medium to the patient-user.

While embodiments of the present invention are described herein with reference to an insulin delivery example for treating diabetes, other embodiments of the invention may be employed for delivering other infusion media to a patient-user for other purposes. For example, further embodiments of the invention may be employed for delivering other types of drugs to treat diseases or medical conditions other than diabetes, including, but not limited to drugs for treating pain or certain types of cancers, pulmonary disorders or HIV. Further embodiments may be employed for delivering media other than drugs, including, but not limited to, nutritional media including nutritional supplements, dyes or other tracing media, saline or other hydration media, or the like. Also, while embodiments of the present invention are described herein for delivering or infusing an infusion medium to a patient-user, other embodiments may be configured to draw a medium from a patient-user.

Figure 1:
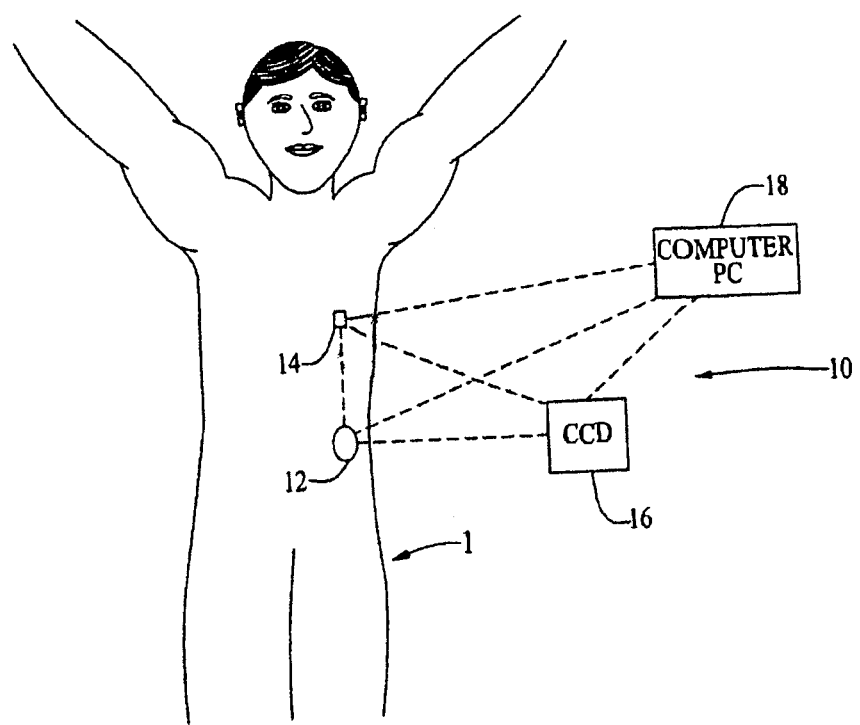
FIG. 1 is a generalized diagram of a delivery system in relation to a human patient-user.

A generalized representation of an infusion medium delivery system 10 is shown in FIG. 1, wherein the system includes a delivery device 12 configured according to an embodiment of the invention described herein. The system 10 may also include other components coupled for communication with the delivery device 12, including, but not limited to, a sensor or monitor 14, a command control device (CCD) 16 and a computer 18. Each of the CCD 16, the computer 18, the sensor or monitor 14 and the delivery device 12 may include receiver or transceiver electronics that allow communication with other components of the system. The delivery device 12 may include electronics and software for analyzing sensor data and for delivering an infusion medium according to sensed data and/or pre-programmed delivery routines. Some of the processing, delivery routine storage and control functions may be carried out by the CCD 16 and/or the computer 18, to allow the delivery device 12 to be made with more simplified electronics. However, in other embodiments, the system 10 may include delivery device 12 that operates without any one or more of the other components of the system 10 shown in FIG. 1.

In the generalized system diagram of FIG. 1, the delivery device 12 and sensor or monitor 14 are secured to a patient-user 1. The locations at which those components are secured to the patient-user 1 in FIG. 1 are provided only as a representative, non-limiting example. The delivery device 12 and sensor or monitor 14 may be secured at other locations on the patient-user 1, and such locations may depend upon the type of treatment to be administered by the system 10. Such other locations may include, but are not limited to, other locations on the patient-user's body, locations on the patient-user's clothing, belt, suspenders, straps, purse, tote or other structure that may be carried by the patient-user.

As described in further detail below, the delivery device 12 contains a reservoir of an infusion medium and delivers the infusion medium into the patient-user's body in a controlled manner. Control instructions and/or data may be communicated between the delivery device 12, the sensor or monitor 14, the CCD 16 and the computer 18. The delivery device 12 may be configured to secure to the skin of a patient-user 1, in the manner of a patch, at a desired location on the patient-user. In such embodiments, it is desirable that the delivery device 12 have relatively small dimensions for comfort and ability to conceal, for example, under a garment.

Examples of patch-like delivery devices are described in U.S. patent application Ser. No. 11/211,095, filed Aug. 23, 2005, which is incorporated herein, in its entirety. A further example of a patch-like delivery device 12 is shown in FIGS. 2-5 herein. The delivery device 12 in FIG. 2 includes a base housing portion 20 that, in some embodiments, may be disposable after one or a number of specified uses, and a durable housing portion 22. The disposable housing portion 20 may support structural elements that ordinarily contact the patient-user's skin or the infusion medium, during operation of the delivery device 12. On the other hand, the durable housing portion 22 may support elements (including electronics, motor components, linkage components, and the like) that do not ordinarily contact the patient-user or the infusion medium during operation of the delivery device 12. Thus, elements in the durable portion 22 of the delivery device 12 are typically not contaminated from contact with the patient-user or the infusion medium during normal operation of the delivery device 12.

In the illustrated embodiment, the disposable portion 20 of the delivery device 12 includes a base 21 that includes or otherwise supports a reservoir retaining portion 24 that houses a reservoir. The durable portion 22 may include a housing that secures onto the base 21 adjacent the reservoir retaining portion 24. The durable portion 22 may house a suitable drive device, such as an electrically operated motor (not shown in FIG. 2), and drive linkage components (not shown in FIG. 2) for driving fluid out of the reservoir. The durable portion 22 also may house suitable control electronics (not shown in FIG. 2) for controlling the operation of the drive device to drive fluid from the reservoir in a controlled manner. Further embodiments may include communication electronics (not shown in FIG. 2) within the durable portion 22, for communicating with the sensor or monitor 14, the CCD 16, the computer 18 and/or other components of the system 10 shown in FIG. 1.

The base 21 of the disposable housing portion 20 has a bottom surface (facing downward and into the page in FIGS. 2 and 3) that is configured to secure to a patient-user's skin at a desired location on the patient-user. A suitable adhesive may be employed at the interface between the bottom surface of the base 21 and the patient-user's skin, to adhere the base 21 to the patient-user's skin. The adhesive may be provided on the bottom surface of the base portion 21, with a peelable cover layer 23 covering the adhesive material. In this manner, a patient-user may peel off the cover layer 23 to expose the adhesive material and then place the adhesive side of the base 21 against the patient-user's skin.

The disposable portion 20 may include a button or other operator 25 for operating a needle inserter device located within the reservoir retaining portion 24. Alternatively, or in addition, reference number 25 may represent an opening, through which an external needle inserter device may operate. Alternatively, or in addition to an operator or opening 25, the needle inserter device may be activated, through a wireless link, from an external controller, such as the CCD 16, sensor or monitor 14 or computer 18. For such embodiments, the CCD 16, sensor or monitor 14 or computer 18 includes a wireless signal transmitter, while the delivery device includes a receiver for receiving a wireless actuation signal and an electronic actuator that is controlled to actuate the needle inserter device, upon receipt of an actuation signal from the CCD 16, sensor or monitor 14 or computer 18. Examples of suitable needle inserter device are described in U.S. patent application Ser. No. 11/211,095, filed Aug. 23, 2005, and U.S. Patent Application Ser. No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. Alternatively, the reservoir retaining portion may include a suitable opening or port for connecting one end of a hollow tube to the reservoir, while the other end of the hollow tube is connected to a hollow needle for piercing the patient-user's skin and conveying the infusion medium from the reservoir into the patient-user, for example, as described with reference to FIG. 2 of U.S. patent application Ser. No. 11/211,095, filed Aug. 23, 2005 and/or as described herein with reference to FIG. 21.

Each of the disposable housing portion 20 and the durable housing portion 22 includes a respective housing shell or housing structure (also referred to herein as an enclosure structure). The durable portion 22 of the delivery device 12 includes a housing shell configured to mate with and secure to the disposable portion 20. The durable portion 22 and disposable portion 20 may be provided with correspondingly shaped grooves, notches, tabs or other suitable features that allow the two parts to easily snap together, by manually pressing the two portions together in a manner well known in the mechanical arts. In a similar manner, the durable portion 22 and disposable portion 20 may be separated from each other by manually applying sufficient force to unsnap the two parts from each other. In further embodiments, a suitable seal, such as an o-ring seal, may be placed along the peripheral edge of the disposable portion 20 and/or the durable portion 22, so as to provide a seal against water between the disposable portion 20 and the durable portion 22.

The durable portion 22 and disposable portion 20 may be made of suitably rigid materials that maintain their shape, yet provide sufficient flexibility and resilience to effectively snap together and apart, as described above. The base 21 material may be selected for suitable compatibility with the patient-user's skin. For example, the disposable portion 20 and the durable portion 22 of the delivery device 12 may be made of any suitable plastic, metal, composite material or the like. The disposable portion 20 may be made of the same type of material or a different material relative to the durable portion 22. The disposable portion and durable portions may be manufactured by injection molding or other molding processes, machining processes or combinations thereof.

The base 21 of the disposable housing portion 20 may be made of a relatively flexible material, such as a flexible silicone, plastic, rubber, synthetic rubber or the like. By forming the base 21 of a material capable of flexing with the patient-user's skin, a greater level of patient-user comfort may be achieved when the base is secured to the patient-user's skin. Also, a flexible base 21 can result in an increase in the site options on the patient-user's body at which the base 21 may be secured.

The disposable portion 20 and/or the durable portion 22 may include an internal sensor (not shown in FIGS. 2 and 3) for connection to a patient-user, for example, through a needle (not shown in FIGS. 2 and 3) or a set of micro-needles for piercing a patient-user's skin when the disposable portion 20 is secured to a patient-user's skin. In such embodiments, a suitable aperture (not shown in FIGS. 2 and 3) may be formed in the base 21, to allow the passage of the sensor needle or micro-needles, when the sensor needle to pierce a patient-user's skin. Alternatively, or in addition, micro-needles may be arranged on or through the adhesive material on the base 21, to pass through the patient-user's skin, when the base 21 is adhered to the patient-user's skin. Alternatively, the durable portion 20 of the delivery device 12 may be connected to an external sensor 14, through a sensor lead, as described in U.S. patent application Ser. No. 11/211,095, filed Aug. 23, 2005. The sensor may include any suitable biological sensing device, depending upon the nature of the treatment to be administered by the delivery device 12. For example, in the context of delivering insulin to a diabetes patient-user, the sensor 14 may include a blood glucose sensor. Alternatively, or in addition, one or more environmental sensing devices may be included in or on the delivery device 12, for sensing one or more environmental conditions.

As described above, by separating disposable elements of the delivery device 12 from durable elements, the disposable elements may be arranged on the disposable portion 20, while durable elements may be arranged within a separable durable portion 22. In this regard, after one (or a prescribed number) of uses of the delivery device 12, the disposable portion 20 may be separated from the durable portion 22, so that the disposable portion 20 may be disposed of in a proper manner. The durable portion 22 may; then, be mated with a new (un-used, pre-filled, refurbished, refilled or re-manufactured) disposable portion 20 for further delivery operation with a patient-user.

A reservoir 26 may be supported by the reservoir retaining portion 24 of the disposable portion 20 in any suitable manner. The reservoir 26 may be a hollow internal volume of the reservoir retaining portion 24, such as, but not limited to, a cylindrical-shaped volume as shown in broken lines in FIG. 3. Alternatively, the reservoir 26 may be a cartridge or generally cylindrical canister having a shape and size to be received within a hollow internal volume of the reservoir retaining portion. The reservoir 26 is configured for containing a fluidic infusion medium.

Figure 2:
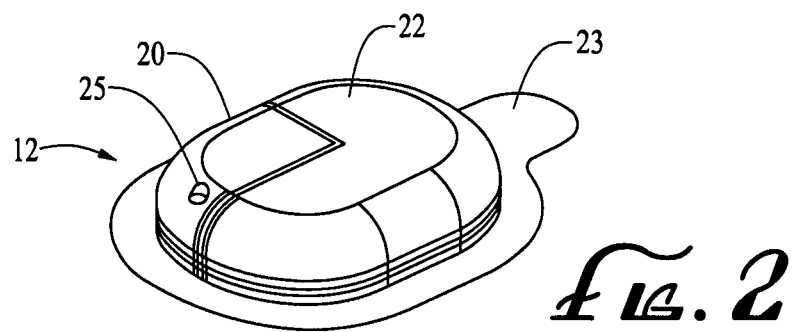
FIG. 2 is a perspective view of a delivery device according to an embodiment of the invention.

The reservoir 26 has a port and a septum. The septum is located in a position at which a hollow needle or cannula may pass through the septum and into a patient-user's skin, when the disposable housing portion 20 is secured to a patient-user's skin, as described below. In other embodiments, the port and septum of the reservoir 26 may be connectable to a patient-user, through an external needle or cannula, through a connector and external tubing, as shown in FIG. 2 of U.S. patent application Ser. No. 11/211,095, filed Aug. 23, 2005, for providing a fluid flow path between the reservoir 26 and the patient-user, when the disposable housing portion 20 is secured to a patient-user's skin. In further embodiments, the port or septum may be used (alternatively or in addition to an outlet port) for filling or re-filling the reservoir 26, for example, but not limited to, inserting a syringe through the septum and passing fluid from the syringe into the reservoir.

The durable portion 22 of the delivery device 12 may include a motor or other force-applying mechanism, for applying a force to the infusion medium within the reservoir 26 to force the fluidic infusion medium out of the reservoir 26 and into the hollow needle or cannula (not shown in FIGS. 2 and 3), for delivery to the patient-user. For example, an electrically driven motor may be mounted within the durable portion 22 with appropriate linkage for causing the motor to operably connect to (through the linkage) a piston plunger within the reservoir and drive the piston plunger in a direction to force the fluidic infusion medium out of the reservoir port and into the patient-user. The motor may be arranged within the durable portion 22 and the reservoir 26 may be correspondingly arranged on the disposable portion 20, such that the operable connection of the motor with the reservoir piston (e.g., through appropriate linkage) occurs automatically upon the patient-user snap fitting the durable portion 22 onto the disposable portion 20 of the delivery device 12.

Figure 4:
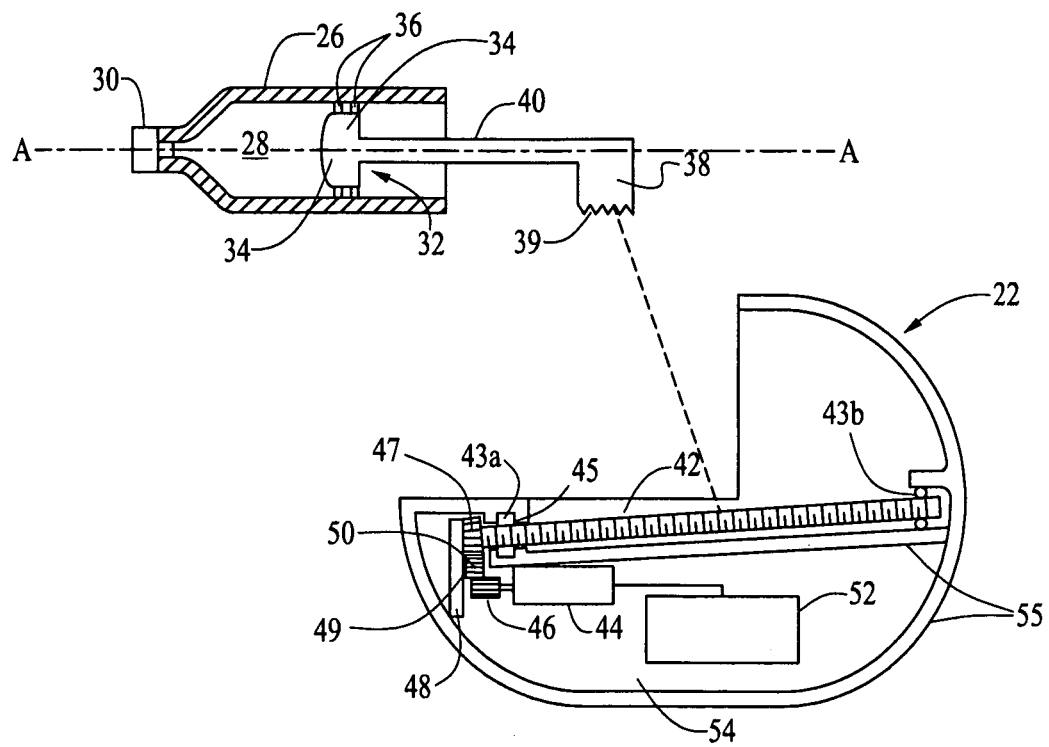
FIG. 4 is a schematic, cross-sectional view of the interior of a reservoir and a durable housing portion of a delivery device according to an embodiment of the invention.

One example of a motor and reservoir configuration is shown in FIG. 4. In the embodiment of FIG. 4, the reservoir 26 (shown in cross-section) is a canister, for example, made of a suitable metal, plastic, ceramic, glass, composite material or the like, and having a hollow interior 28 for containing a fluidic infusion medium. For example, the canister may be formed of a plastic material referred to as TOPAS (trademark of Ticona, a subsidiary of Celanese Corporation), such as described in U.S. patent application Ser. No. 11/100,188, filed Apr. 5, 2005 (Publication No. 2005/0197626), the contents of which is incorporated herein in its entirety.

Figure 3:
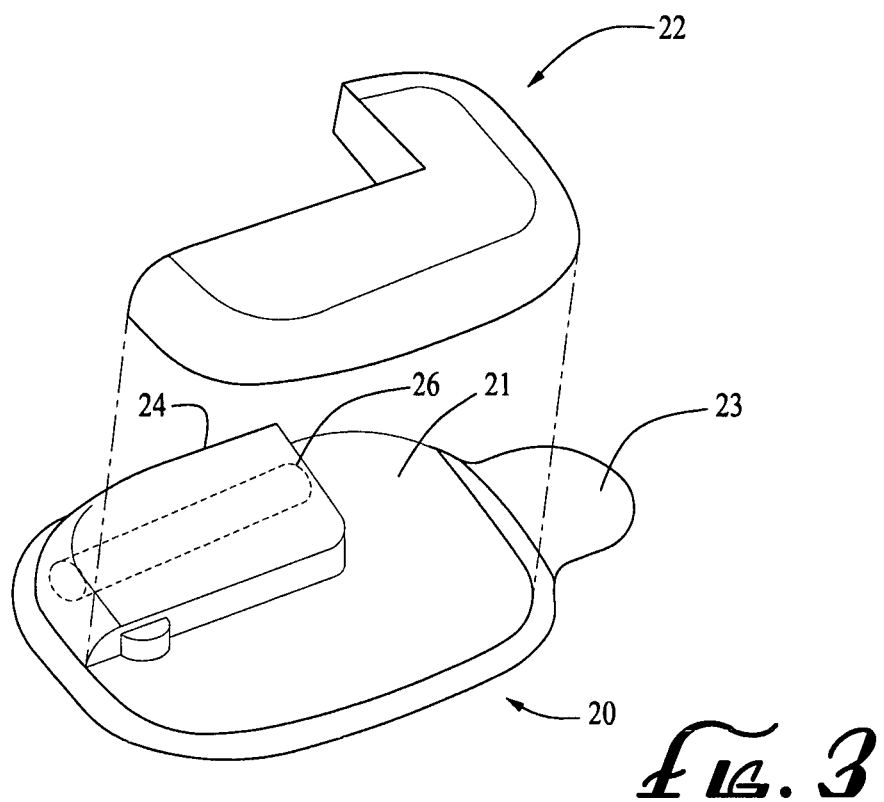
FIG. 3 is a perspective view of a durable portion and a disposable portion of the delivery device of FIG. 2, with the durable portion separated from the disposable portion.

The canister reservoir 26 in FIG. 4 may be configured to fit within and be removable from a correspondingly-shaped opening and volume in the reservoir retaining portion 24 shown in FIG. 3. In such embodiments, the canister reservoir 26 and reservoir retaining portion 24 may include one or more mating protrusions, grooves, indentations and/or non-circular cross-section that restrain the canister reservoir 26 from rotating about the axis A relative to the reservoir retaining portion 24, once the canister reservoir 26 is fitted within the reservoir retaining portion 24. In further embodiments, a canister reservoir 26 may be permanently fixed within the interior volume of the reservoir retaining portion 24.

By supporting a canister reservoir 26 in a manner that allows the reservoir 26 (and piston plunger 32) to be removed and replaced relative to the remainder of the disposable portion 20, a user may replace a spent canister reservoir 26 with a new (un-used, pre-filled, refurbished, refilled or re-manufactured) canister reservoir 26 (and piston plunger 32), while the disposable portion remains secured to the patient-user's skin. In this manner, the same disposable portion 20 may be used for multiple new reservoirs 26 and, then, disposed of after a prescribed number of new or re-filled reservoirs have been used on the disposable portion 20, while the same durable portion 22 may be used for multiple disposable portion 20 replacements.

As described above, in yet further embodiments, the reservoir 26 may be formed unitarily with the reservoir retaining portion 24, for example, as a shaped, hollow interior of the reservoir retaining portion 24. In such embodiments, the hollow interior of the reservoir retaining portion 24 may be coated or otherwise lined with a suitable metal, plastic, plastic, TOPAS (trademark of Ticona, a subsidiary of Celanese Corporation), ceramic, glass, composite material or the like. Alternatively, or in addition, the retaining portion 24, itself, may be made of a suitable metal, plastic, plastic, TOPAS (trademark of Ticona, a subsidiary of Celanese Corporation), ceramic, glass, composite material or the like.

The reservoir 26 includes a septum 30 that can be pierced by a hollow needle or cannula to provide a hollow flow path from the interior 28 of the reservoir 26 to the patient-user. Examples of mechanisms that may be used for moving a hollow needle through a septum of a reservoir are described in U.S. patent application Ser. No. 11/211,095, filed Aug. 23, 2005, and U.S. Patent Application Ser. No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006. Alternatively, or in addition, the septum 30 may include a surface that is exposed through a wall of the reservoir retaining portion, for refilling the reservoir 26 or withdrawing infusion medium from the reservoir 26, for example, by piercing the exposed surface of the septum with a syringe, hollow needle or cannula. The septum 30 may be formed of a suitable material, such as, but not limited to, rubber, silicone rubber, polyurethane or other materials that may be pierced by a needle and form a seal around the needle.

Figure 5:
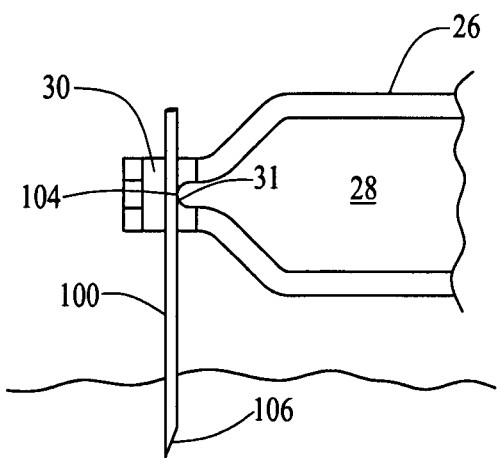
FIG. 5 is a schematic, cross-sectional view of a portion of a reservoir, showing an arrangement of a hollow needle or cannula piercing the reservoir septum and a patient-user's skin.

With reference to FIG. 5, the septum 30 may be configured such that a hollow needle or cannula 100 may be passed through the septum to create a fluid flow path between the interior 28 of the reservoir 26 and a patient-user 1. In particular, when the hollow needle or cannula 100 is passed through the septum 30, a side opening 104 in the hollow needle or cannula 100 may be aligned with a channel or indentation 31 in the septum 30 to form a fluid flow path between the hollow interior of the needle and the interior 28 of the reservoir 26. The hollow needle or cannula 100 includes a patient-end opening 106, to form a fluid flow path between the hollow interior of the needle or cannula 100 and a patient-user 1, upon the sharp end of the needle or an open end of the cannula being inserted in a patient-user's skin. Alternatively, an injection site for inserting a hollow needle or cannula into a patient-user and coupling the needle or cannula in fluid flow communication with the reservoir, as described below with reference to the injection site 132 in FIG. 8, may be employed in the embodiment of FIGS. 1-5. In further embodiments, the injection site may comprise a set of hollow micro-needles arranged to pierce a patient-user's skin, when the disposable housing portion 20 is secured to the patient-user's skin, wherein the micro-needles are connected in fluid-flow communication (for example, through a manifold structure) to the reservoir 26.

A piston plunger 32 is moveable within the interior of the reservoir, for changing the volume of the fluid-containing portion of the interior 28 of the reservoir 26. When a hollow needle or cannula is passed through the septum 30 (or a set of micro-needles are arranged in fluid flow communication with the reservoir) to form a fluid flow path from the reservoir to a patient-user, as described herein, infusion medium inside of the reservoir 26 may be expelled from the reservoir, to the patient-user, in response to a force applied by the piston plunger 32.

The piston plunger 32 extends partially into the interior of the reservoir 26 from the opposite side of the canister relative to the septum 30. The piston plunger 32 may be made of a suitably rigid material, such as but not limited to metal, plastic, ceramic, glass or composite material, and has a head 34 that has an outside diameter of slightly less than the inside diameter of the interior 28 of the reservoir 26. Alternatively, the piston plunger 32 may be made of a compressible material (such as, but not limited to, an elastically compressible plastic, rubber, silicone, or the like) and may be slightly larger in diameter than the inside diameter of the interior 28 of the reservoir 26, so as to be compressed sufficiently to fit within the interior 28 of the reservoir 26. One or more seals, such as but not limited to o-ring type seals 36, may be arranged within annular grooves provided on the piston plunger head 34. The o-ring seals 36 may be made of any suitable material, including, but not limited to rubber, plastic, metal, composite material or the like, where such o-rings provide a sealing function for inhibiting the leakage of infusion medium from the piston-plunger end of the reservoir 26. The materials from which the canister portion of the reservoir 26, piston plunger 32 and seal(s) 36 are made are preferably selected for suitable strength and durability characteristics, as well as compatibility with the infusion medium.

The piston plunger 32 and the interior surface of the reservoir 26 may include an anti-rotation structure, such as, but not limited to, one or more mating protrusions, grooves, indentations similar to those described below with respect to FIG. 10 and/or non-circular cross-section that restrain the piston plunger 32 from rotating about the axis A relative to the reservoir 26. Alternatively, the anti-rotation feature may include one or more seals, such as the seal(s) 36, provided that such seal(s) have sufficient frictional resistance with the interior surface of the reservoir 26 to inhibit rotation of the piston plunger 32 about the axis A, relative to the reservoir 26. For embodiments in which one or more protrusions and mating grooves are provided on the piston plunger 32 and interior surface of the reservoir 26, the protrusions and grooves may be formed with sufficiently slowly arched or curved surfaces (instead of abrupt angles or corners), to allow a seal to be readily placed over the surfaces and seal against the piston plunger 32 and interior surface of the reservoir 26. In yet further embodiments, an anti-rotation structure may be provided on the piston shaft 40 and may include any suitable structure for engaging a surface of the durable housing portion 22 or disposable housing portion 20 (or other suitable surface structure supported by the durable housing portion 22 or the disposable housing portion 20) and inhibiting rotation of the piston shaft 40 about the axis A.

The piston plunger 32 in FIG. 4 includes an engagement portion 38, located external to the interior 28 of the reservoir 26 and connected by a plunger shaft 40 to the plunger head 34. The piston plunger 32 is configured to be moveable in the axial direction A of the reservoir 26. The fluid-containing portion of the interior volume 28 of the reservoir 26 varies, with movement of the piston plunger 32 in the axial direction A of the reservoir 26. The engagement portion 38 is provided with keys, key slots or threads 39 (hereinafter referred to as threads) that are configured to operatively engage corresponding key slots, keys or threads (hereinafter, referred to as threads) on a lead shaft 42. As described in more detail below, when the engagement portion 38 is operatively engaged with the lead shaft 42 and a drive motor 44 rotates the lead shaft 42, the piston plunger 32 will move axially within the reservoir 26.

The anti-rotation structure described above inhibits the piston plunger 32 from rotating about the axis A. Accordingly, the piston plunger 32 may be arranged in, and inhibited from rotating away from, a position in which the threaded surface 39 of the engagement portion 38 faces a direction that allows the surface 39 to automatically align with and readily come into operable engagement with the lead shaft 42 when the durable portion 22 and the disposable portion 20 are arranged together for coupling.

The lead shaft 42 may be supported for rotation on the durable portion 22 of the delivery device 12. For example, one or more bearings or other suitable structure may be fixed in the durable portion for supporting the lead shaft 42 for rotation about its longitudinal axis. In the embodiment of FIG. 4, the lead shaft 42 is supported at two locations by two rotary bearings 43a and 43b. In other embodiments, the lead shaft 42 may be supported in more than two locations by more than two bearings or may be supported in a cantilevered fashion at one location by a single bearing 43a or 43b. A portion of the length of the lead shaft 42 may be exposed for engagement with the engagement portion 38 of the piston plunger 32. The lead shaft 42 extends through an opening in the durable portion 22 such that a further portion of the lead shaft 42 is located within the enclosed interior 54 of the durable portion 22, for engagement with drive linkage, as described below. One or more seals 45 may be located around the lead shaft 42, between the exposed portion of the lead shaft and the further portion of the lead shaft located in the durable portion 22. In this manner, the seal(s) 45 may inhibit fluid from entering the opening in the durable portion 22 through which the lead shaft 42 extends. The seal(s) 45 may be made of any suitable seal material, including, but not limited to silicone or other flexible plastic, metal, ceramic, composite material or the like. In further embodiments, the seal(s) 45 may comprise a material and/or seal configuration that provides a liquid-tight seal, but allows the passage of air to allow equalization of pressure between the interior 54 of the durable housing portion 22 and the environment exterior of the durable housing portion 22. In yet other embodiments, a pressure equalization port opening may be provided in any suitable location of the durable housing portion, to provide air-flow communication between the interior 54 and exterior of the durable housing portion. In such embodiments, the air-flow communication port may be covered with a material that allows the passage of air, but inhibits the passage of water or other liquids.

A drive motor 44 is mechanically coupled to the lead shaft 42, to drive the lead shaft in a rotary motion about its longitudinal axis, in a controlled manner. The motor 44 may be coupled to the lead shaft 42 through one or more suitable gears, belts, chains, drive shafts or other linkage structure. The linkage structure may be configured to provide a torque conversion, for example, to increase torque and decrease rotational speed at the lead shaft, relative to the torque and speed output of the motor 44. Accordingly, the motor 44 may produce relatively high-speed rotational motion, which may be converted through the linkage structure to a lower speed of rotation, but higher torque applied to the lead shaft. In the embodiment illustrated in FIG. 4, the motor 44 includes a drive gear 46, while the shaft 42 is provided with an engagement gear 47. A linking gear 48 is arranged between the drive gear 46 and the engagement gear 47, to convey rotary drive force from the motor 44 to the shaft 42. The linking gear 48 in FIG. 4 includes hub portion 49 for engaging the drive gear 46, and a main portion 50 for engaging the engagement gear 47. The hub portion 49 is fixed to the main portion 50 and has a smaller diameter than the main portion 50. In other embodiments, a linking gear 48 may be arranged such that a smaller diameter hub portion engages the engagement gear 47, while a larger diameter main portion engages the drive gear 46. In yet further embodiments, additional gears may be interposed between some or each of the gears 46, 47 and 48, to convey rotational motion from the motor 44 to rotational motion of the lead shaft 42. In yet further embodiments, the linking gear 48 may be eliminated and the drive gear 46 may be arranged to directly engage the engagement gear 47. In yet further embodiments, other linkage structure may be employed to operatively link the motor 44 to the lead shaft 42.

The drive gear 46, the linking gear 47 and engagement gear 48 form a gear train for transferring motor drive force from the motor 44 to the lead shaft 42. In this manner, as the motor rotatably drives the motor drive shaft, the gear train transfers the motor drive force to rotate the lead shaft 42. When the piston plunger 32 is engaged with the lead shaft 42, rotation of the lead shaft 42 causes the engagement portion 38 of the piston plunger 32 to ride along a portion of the threaded length of the lead shaft 42. In this manner, the rotation of the lead shaft 42 is transferred to an axial movement of the piston plunger 32, when the piston plunger is engaged with the lead shaft 42. The available length of travel of piston plunger 32 is dependant upon the length of the threaded portion of the lead shaft 42, the length of the piston plunger shaft 40 and the starting location of the engagement portion 38 of the piston plunger along the threaded length of the lead shaft 42.

The lead shaft 42 in FIG. 4 may be provided with threads along most or all of the length of the exposed portion of the shaft, to allow operable engagement of the threads on the engagement portion 38 to the corresponding threads on the lead shaft 42 at any location along the length of the exposed portion of the lead shaft 42. To further assist the operable engagement of the threads on the engagement portion 38 to the corresponding threads on the lead shaft 42, the engagement portion 38 may be provided with a arcuate surface on which the threads are arranged, as shown in FIG. 6a. The threaded arcuate surface of the engagement portion 38 may extend around one half or less (180 degrees or less) of the circumference of the lead shaft 42, when the engagement portion 38 is engaged with the lead shaft 42 (i.e., when the durable housing portion and disposable housing portion are engaged as shown in FIG. 2). In further embodiments, the threaded arcuate surface of the engagement portion 38 may extend around a little more than one half (more than 180 degrees) of the circumference of the lead shaft 42 and may be composed of sufficiently resilient, flexible material to provide a snap-fit with the lead shaft, when the engagement portion 38 is engaged with the lead shaft 42 (i.e., when the durable housing portion and disposable housing portion are engaged as shown in FIG. 2).

In other embodiments as represented in FIG. 6, the piston plunger shaft 40 may be provided with teeth (or threads) along its length and the lead shaft 42 may have a disk-shaped threaded head portion 41 that may be relatively short in length in the axial direction A. The threaded head portion 41 has threads on its outer peripheral surface to engage the teeth (or threads) of the piston plunger shaft 40, for example, in a rack and pinion type of an arrangement, wherein the piston plunger shaft 40 may include a toothed rack and the threaded head portion 41 may function as a pinion gear. In embodiments as shown in FIG. 6, the piston plunger shaft 40 may be provided with an arcuate surface 51 on which the teeth (or threads) are located. The arcuate surface 51 extends along the longitudinal dimension of the piston plunger shaft 40, outside of the interior portion 28 of the reservoir 26 and arcs partially around the axis of the lead shaft 42, to engage the head portion 41, when the durable housing portion and the disposable housing portion are engaged as shown in FIG. 2. The radius of the arcuate surface 51 may approximate the radius of the disk-shaped head 41, to allow the head 41 to readily, operatively engage the piston plunger shaft and to increase the surface area of engagement between those components, when the durable housing portion and disposable housing portion are engaged as shown in FIG. 2.

Similar to the arcuate surface of the engagement portion 38 in FIG. 4 described above, the arcuate surface 51 of the piston plunger shaft 40 in FIG. 6 may extend around one half or less (180 degrees or less) of the circumference of the lead shaft 42, when the piston plunger shaft 40 is engaged with the lead shaft 42 (i.e., when the durable housing portion and disposable housing portion are engaged as shown in FIG. 2). In further embodiments, the arcuate surface 51 of the piston plunger shaft 40 may extend around a little more than one half (more than 180 degrees) of the circumference of the lead shaft 42 and may be composed of sufficiently resilient, flexible material to provide a snap-fit with the lead shaft, when the piston plunger shaft 40 is engaged with the lead shaft 42 (i.e., when the durable housing portion and disposable housing portion are engaged as shown in FIG. 2).

In the embodiments of FIGS. 4 and 6, one of the lead shaft 42 or the piston plunger shaft 40 includes a threaded portion extending a length along the direction of axis A, beyond the length in the direction of axis A of the fluid containing portion 28 of the reservoir 26. The piston plunger shaft 40 may be provided with threads along most or all of the length of the exposed portion of the shaft, to allow operable engagement with the lead shaft 42 or threaded head portion 41, at any location along the length of the exposed portion of the piston plunger shaft 40.

The motor 44, lead shaft 42 and any linkage between the motor and lead shaft may be supported by the durable portion 22 of the delivery device in a location at which the threaded portion of the shaft 42 engages the threaded portion of the piston plunger 32, as shown in FIGS. 4 or 6. In this manner, when the durable portion 22 is arranged to be snap fitted onto the disposable portion 20, the threaded portion of the shaft 42 operatively engages the threaded portion of the piston plunger 32 without requiring further user manipulation of the elements.

While not shown in FIG. 4, the motor 44 may be provided with electrical terminals for connection to a motor control circuit 52. The motor control circuit 52 may be mounted within the durable portion 22 of the delivery device, for controlling the operation of the motor according to a desired infusion delivery program or profile. A delivery program or profile may be stored within a suitable electronic storage medium (not shown) located within the durable portion 22 and/or may be communicated to the delivery device 12 from other sources, such as a CCD 16 or a computer 18 (as shown in FIG. 1). In such embodiments, the delivery program or profile may be employed by the motor control circuit 52 to control the operation of the motor 44 in accordance with the delivery program or profile. Alternatively or in addition, the motor control circuit 52 may control the motor 44 to deliver one or more discrete volumes of infusion medium in response to delivery demand control signals generated within the device 12 or communicated to the device 12 from other sources, such as a CCD 16, sensor or monitor 14 or a computer 18 (as shown in FIG. 1).

The durable portion 22 may contain additional electronic circuitry (not shown) for communication with external devices such as the CCD 16 or computer 18, for storage of sensor data or other data, for processing and control functions, or for other functions. The durable portion 22 may have a user interface (not shown) including one or more buttons, electronic display, or the like, to allow a user to access data and/or input data or instructions to control electronic circuitry within the durable portion 22.

In some embodiments, the durable portion 22 may contain a battery, high energy capacitor or other electronic power source (not shown) for providing electrical power to the motor 44, motor control circuit 52 and other electronic circuitry contained in the durable portion 22. In such embodiments, the battery, high energy capacitor or other electronic power source may be rechargeable through a recharge connector (not shown) provided on the durable portion 22. In other embodiments, a battery, capacitor or other electronic power source (not shown) may be supported on the disposable portion 20 and connectable to the motor 44, motor control circuit 52 and other electronic circuitry in the durable housing portion, through electrical connectors that make an electrical connection upon the durable portion 22 being coupled to the disposable portion 20, without additional manual manipulation. Such electrical connectors may include one or more pairs of conductive pads, where each pair of pads is connected to opposite poles of the power source and located on any suitable surface of the disposable portion 20 that engages a corresponding surface on the durable portion 22, when the durable portion 22 is coupled to the disposable portion 20. In such embodiments, the corresponding surface of the durable portion 22 includes one or more corresponding pairs of conductive pads that are electrically connected to the motor 44, motor control circuit 52 and other electronic circuitry in the durable housing portion and are arranged to engage the conductive pads on the disposable portion, when the durable portion 22 is coupled to the disposable portion 20.

The durable portion 22 includes an interior volume 54 that contains the motor 44, gears 46-48, motor control circuit 52, other electronic circuitry and, in some embodiments described above, a power source. To protect those electrical and mechanical components from certain environmental conditions (such as, but not limited to, moisture, air, biological or medical fluids), the interior volume 54 of the durable portion 22 may be suitably sealed from the external environment by the housing structure 55 that forms the durable portion 22 and the seal(s) 45 for the opening through which the lead shaft 42 extends. Accordingly, the housing structure of the durable portion 22 and the seal(s) 45 may form a suitable moisture-tight seal, air-tight seal and/or hermetic seal, to protect the electronic components located in the interior volume 54 and/or separate those components from environmental, medical or biological materials to which the disposable portion 20 is exposed during normal operation. The gear train composed of gears 46, 47 and 48, may be included in the sealed interior volume 54, to protect and/or separate those mechanical components from environmental or biological materials, as well.

As discussed above, in the arrangement illustrated in FIGS. 2, 3, 4 and 6, the durable portion 22 may be snap fitted onto the disposable portion 20, where the threaded portion of the lead shaft 42 automatically engages the threaded portion of the piston plunger 32 without requiring further user manipulation of the elements. In the embodiment of FIG. 4, the threaded surface 39 of an engagement portion 38 of the piston plunger 32 may have an arcuate surface that curves around a portion of the longitudinal axis of the lead shaft 42. By providing the surface of the engagement portion 38 of the piston plunger 32 with an arcuate shape that curves around a portion of the longitudinal axis of the lead shaft 42, the surface area of the surface 39 that engages the lead shaft 42 may be increased. In addition, the curvature of the surface 39 of the engagement portion 38 around a portion of the longitudinal axis of the lead shaft 42 can help to inhibit inadvertent separation of the engagement portion 38 and the lead shaft 42, once the engagement portion 38 is engaged with the lead shaft 42. The curvature of the surface 39 also may allow the engagement portion 38 to easily align with and operably engage the lead shaft 42, by bringing the lead shaft 42 into contact with the engagement portion 38 as a consequence of the manual operation of coupling the durable portion 22 to the disposable portion 20.

As described above, when the durable portion 22 and the disposable portion 20 are fitted together with the lead shaft 42 engaging the engagement portion 38 of the piston plunger 32, the motor 44 may be controlled to rotatably drive the lead shaft 42 and, thus, move the piston plunger 32 in the axial direction A of the reservoir 26. When the volume 28 of the reservoir 26 is filled with an infusion medium and a hollow needle or cannula is positioned in the septum 30 of the reservoir to form a fluid flow path between the reservoir 26 and a patient-user, the piston plunger 32 may be controlled to move in the axial direction A, toward the septum 30 end of the reservoir 26, to force infusion medium from the reservoir volume 28, through the hollow needle or cannula and to the patient-user.

Once the reservoir 26 has been sufficiently emptied or otherwise requires replacement, the patient-user may simply unsnap and remove the durable portion 22 from the disposable portion 20 of the delivery device 12 and replace the disposable portion 20 (including the reservoir) with a new disposable portion having a prefilled or re-filled reservoir 26. The durable portion 22 may be snap fitted onto the new disposable portion and the delivery device (including the new disposable portion) may be secured to the patient-user's skin, as described above.

In further embodiments in which the reservoir 26 includes a reservoir canister that fits within a hollow interior of the reservoir retaining portion 24, the canister may be removed from the retaining portion 24 and replaced with a new canister, to allow the disposable portion 22 to be remain in place on a patient-user for more than one reservoir depletion period. In such embodiments, the reservoir canister may be replaced one or more times during the operable life of the disposable portion 20 and the disposable portion 20 may be removed from the patient-user and replaced with a new or remanufactured disposable portion 20, for example, after a predefined number of reservoir canister replacement operations.

The drive motor 44 in FIG. 4 may include any suitable rotary drive device that converts electrical power to mechanical, rotary motion. Examples of a suitable rotary drive motor 44 include, but are not limited to, a DC motor, flat or pancake DC motor, servo motor, stepper motor, electronically commutated motor, rotary piezo-electrically actuated motor, and the like. In further embodiments, the drive motor 44 may include a bender or linear actuator in combination with an escapement wheel arrangement, to rotatably drive the lead shaft 42. For example, a drive device for rotatably driving the lead shaft 42 may include a piezo-electrically actuated bender and escapement wheel arrangement, a thermally actuated bender and escapement wheel arrangement, a shape memory alloy wire and escapement wheel arrangement, an electronically actuated solenoid and escapement wheel arrangement, or the like.

Escapement wheel arrangements operable with bender or linear actuators in accordance with example embodiments of the present invention are described with reference to FIGS. 7a-7c. As shown in FIG. 7a, an escapement wheel 60 is supported for rotation around an axis Al (extending into the page), in the direction of arrow 62. The escapement wheel 60 has an outer peripheral edge provided with serrations or teeth 64. Each tooth 64 includes a sloped surface 66 arranged at an obtuse angle relative to an axial direction of the wheel 60 and a catch surface 65 in a substantially axial direction of the wheel. A drive pawl 68 is located adjacent to the escapement wheel 60 and at least partially between two of the teeth on the escapement wheel. The drive pawl 68 is supported for movement in a generally linear direction, as represented by the double arrow 69, between a start position S and an end position E.

The drive pawl 68 has a drive surface 70 for engaging the catch surface 65 of an adjacent tooth 64 on the escapement wheel 60, when the drive pawl 68 is moved in a direction from the start position S to the end position E. The drive pawl 68 has a further surface 71 facing away from the drive surface 70 and configured for riding over the sloping surface 66 of a tooth 64 on the escapement wheel 60, when the drive pawl is moved in a return direction from the end position E to the start position S. The further surface 71 of the drive pawl 68 may be sloped at an angle relative to the radial direction of drive wheel, to assist the drive pawl 68 in riding over the sloping surface 66 of a tooth 64 of the escapement wheel.

As described in more detail below, the drive pawl 68 is coupled to a bender or linear motion actuator to selectively drive the drive pawl 68 from the start position S to the end position E. With each motion of the drive pawl 68 from the start position S to the end position E, the surface 70 engages the catch surface 65 of a tooth 64 on the escapement wheel and rotates the escapement wheel 60 a small distance. A bias member 72 is operably coupled to the drive pawl 68, to bias the drive pawl 68 in a return direction, to return the drive pawl 68 to the start position. The bias member 72 may include a spring as shown in FIG. 7a or other suitable mechanism for providing a bias force to return the drive pawl 68 to the start position, including, but not limited to a permanent magnet, electromagnet, electronic or thermal linear actuator, shaped memory allow actuator, or the like. In the illustrated embodiment, the bias member 72 is a coil spring having one end coupled to the drive pawl 68 and another end coupled to a fixed surface, for example, a fixed surface of a wall or other fixed structure of or within the durable portion 22 of the drive mechanism 12 described above.

A further pawl 74 may be provided to inhibit back rotation of the escapement wheel 60 in the direction opposite to the direction of arrow 62. For example, the further pawl 74 may be located adjacent the escapement wheel 60 and at least partially between two of the teeth on the escapement wheel. The further pawl 74 has a surface 76 for engaging the catch surface 66 of an adjacent tooth 64 on the escapement wheel 60, to inhibit rotary motion of the escapement wheel 60 in the direction opposite to the direction of arrow 62.

The pawl 74 has a further surface 77 facing opposite to the surface 76, configured for riding over the sloping surface 66 of a tooth 64 on the escapement wheel 60, when the escapement wheel is driven in the rotary direction of arrow 62 by action of the drive pawl 68. The surface 77 of the pawl 74 may be angled relative to the radial direction of the drive wheel, to assist the pawl 74 in riding over the sloping surface 66 of a tooth 64 of the escapement wheel. The pawl 74 may be supported for pivotal motion about a pivot point 78 in the direction of double arrow 79, to allow the surface 77 of the pawl 74 to pivot in a direction away from the escapement wheel, to further assist the pawl 74 in riding over the sloping surface 66 of a tooth 64 of the escapement wheel.

A bias member 80 may be arranged to bias the surface 76 of the pawl 74 toward the escapement wheel, to return the pawl 74 to a position in which the surface 76 engages the catch surface 65 of a tooth 64, after the pawl 74 has ridden over the sloping surface 66 of an adjacent tooth 64 of the escapement wheel. The bias member 80 may include a spring as shown in FIG. 7a or other suitable mechanism for providing a bias force to return the pawl 74 to the position in which the pawl surface 76 engages the catch surface 65 of a tooth 64, including, but not limited to a permanent magnet, electromagnet, electronic or thermal linear actuator, shaped memory allow actuator, or the like. In the illustrated embodiment, the bias member 80 includes a coil spring having one end coupled to the pawl 74 and another end coupled to a fixed surface, for example, a fixed surface of a wall or other fixed structure of or within the durable portion 22 of the drive mechanism 12 described above. In further embodiments, a leaf spring or other suitable spring structure may be employed, instead of a coil spring. For example, a spring may be located around or within the pivot point 78 of the pawl 74 for effecting the bias force described above.

As described above, the drive pawl 68 is coupled to a bender or linear motion actuator to selectively drive the drive pawl 68 and cause the escapement wheel to rotate a small distance with each motion of the drive pawl 68 from the start position S to the end position E. A bender or linear actuator may include a piezoelectric bender or piezoelectric actuator, a thermally actuated bender, a shape memory alloy wire, an electronically actuated solenoid, or the like. Such actuators for providing small, generally linear movements in response to the application of an electrical power signal are known.

As shown in FIG. 7b, a bender actuator 82 may be configured to include a connector end 84 that is provided with a lateral motion represented by arrow 86 relative to a major axis $A_2$ of the actuator body, when a power signal is applied to the actuator. Alternatively, as shown in FIG. 7c, a linear actuator 88 may be configured to include a connector end 90 that is provided with a longitudinal motion represented by arrow 92 relative to a major axis $A_3$ of the actuator body, when a power signal is applied to the actuator. A bender actuator as shown in FIG. 7b, for providing lateral motion, may be coupled to the drive pawl 68 at a connection location 96. The connection location 96 for a bender actuator may be on a surface of the drive pawl 68 that is substantially perpendicular to the drive surface 70. Alternatively, a linear actuator as shown in FIG.

7c, for providing longitudinal motion, may be coupled to the drive pawl 68 at a connection location 98. The connection location 98 for a linear actuator may be on a surface of the drive pawl 68 that is substantially parallel to the drive surface 70. In that manner, a bender or a linear actuator as shown in FIGS. 7b and 7c may be employed to selectively move the drive pawl 68 from the start position S to the end position E and, thus drive the escapement wheel 60 in a rotary manner. In yet further embodiments, the drive pawl 68 may be eliminated and the bender or linear actuator may be arranged to directly engage the catch surfaces of the teeth on the escapement wheel 60.

The escapement wheel 60 may be configured to rotate the rotary distance of one tooth for each movement of the drive pawl 68 from the start position S to the end position E. In further embodiments, the drive pawl 68 may be configured to cause the escapement wheel 60 to rotate a rotary distance of a pre-defined number of teeth greater than one tooth, for each movement of the drive pawl 68 from the start position S to the end position E. The escapement wheel 60 may be coupled to the lead shaft 42, to rotate the lead shaft 42 with rotation of the escapement wheel 60. In one embodiment, the lead shaft 42 may be connected in axial alignment directly to the escapement wheel 60, such that the rotary axis $A_1$ of the escapement wheel is in alignment with the longitudinal axis of the lead shaft 42. In other embodiments, the escapement wheel 60 may be coupled, in axial alignment, with any one of the drive gear 46, engagement gear 47 or linking gear 48 shown in FIG. 4, to transfer rotary motion of the escapement wheel 60 to the lead shaft 42. In yet further embodiments, other suitable gear and linkage arrangements may be employed for transferring rotary motion of the escapement wheel 60 to the lead shaft 42.

The use of bender or linear actuators with escapement wheel arrangements as described above may provide certain advantages over electric motor and linkage arrangements, in that the bender or linear actuators can provide a repeatable, controlled, step-like response to an electrical power signal. In the context of driving a delivery device for delivering a medication to a patient-user, the ability to accurately control the drive response can provide significant advantages, for example, in administering accurate quantities, small quantities at accurate levels and accurate recording of delivered quantities of the medication. In addition, bender or linear actuators with escapement wheel arrangements can be made relatively small and flat and can, therefore, improve the ability to form the delivery device 12 with a relatively small and flat shape. In addition, bender or linear actuators with escapement wheel arrangements can operate with relatively low power requirements, thus prolonging the operational life of the power source and allowing smaller power sources to be employed, thus, allowing further reductions in the size of the delivery device.

Other types of drive devices may be coupled to an escapement wheel 60, as shown in FIG. 7d, to provide a controlled, step-like response. For example, in the embodiment shown in FIG. 7d, the escapement wheel 60 has one tooth and is coupled to the lead shaft 42 as described above, while a second toothed wheel 99 is operatively coupled to the lead shaft 27, for example, through a suitable linkage structure as described herein. The escapement wheel 60 may be driven by any suitable rotary drive source, including, but not limited to a DC motor, flat or pancake DC motor, servo motor, stepper motor, electronically commutated motor, rotary piezo-electrically actuated motor, and the like. While the escapement wheel 60 in FIG. 7d is provided with a single tooth to effect a rotation of the second wheel 99 a rotary distance of a single tooth for each complete rotation of the escapement wheel 60, other embodiments may employ an escapement wheel 60 having two teeth (or another pre-defined number of teeth) for effecting a rotation of the second wheel 99 a rotary distance of two teeth (or the pre-defined number of teeth) for each complete rotation of the escapement wheel 60.

The above embodiments involve various manners of conveying a drive force to the lead shaft 42, to rotate the lead shaft 42 and drive a piston plunger 32 within the reservoir 26. Further embodiments may employ other mechanisms for driving a plunger within a reservoir, to selectively deliver infusion medium from the reservoir.

For example, FIGS. 8-12 show a further embodiment of a delivery device, which includes a disposable portion 120 and a durable portion 122. The disposable portion has a reservoir retaining portion 124 in which a reservoir 126 is located. The disposable portion 120, durable portion 122, reservoir retaining portion 124 and reservoir 126 may be similar to the disposable portion 20, durable portion 22, reservoir retaining portion 24 and reservoir 26 described above with respect to FIGS. 2-6. However, the reservoir 126 in FIGS. 8-12 employs a rotatable plunger shaft 127 located within the reservoir interior 128, instead of the arrangement shown in FIGS. 2-6 that employs a piston plunger shaft 40 that extends, lengthwise, a distance beyond the medium-containing portion of the interior 28 of the reservoir 26 by a distance at least as great as the distance that the piston head 34 moves over the full period of use of the reservoir. Accordingly, the overall length of the reservoir and internal shaft of FIGS. 8-12 may be smaller relative to the overall length of the reservoir and external shaft of FIGS. 2-6, for a given reservoir volume.

The reservoir 126 in FIGS. 8 and 9 may include a septum 130, similar to the septum 30 described above with respect to FIG. 5. The septum 130 may include a surface 131 that is exposed through a wall of the reservoir retaining portion 124, for refilling the reservoir 126 or withdrawing infusion medium from the reservoir 26, for example, by piercing the exposed surface of the septum with a syringe.

An injection site 132 may be located within the disposable portion 120, adjacent the reservoir 126 and connected in fluid flow communication to the interior of the reservoir 126. The injection site 132 may employ a mechanism for inserting a hollow needle or cannula into a patient-user, after the disposable portion 120 is secured to the patient-user and coupling the needle or cannula in fluid flow communication to the interior of the reservoir 126. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application Ser. No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006.

The rotatable shaft 127 is threaded along its length within the interior of the reservoir 126. A moveable plunger head 134 is located within the interior of the reservoir 126 and is threaded and engaged with the rotatable shaft 127. In particular, the plunger head 134 has a threaded channel that has threads of a pitch and diameter to engage and mate with the threads of the rotatable shaft 127. By rotating the shaft 127 without rotating the plunger head 134, the plunger head is moved along the length of the shaft 127, within the interior of the reservoir 126. In this manner, the shaft 127 may be rotated to drive the plunger head 134 and force the infusion medium from the reservoir 126 to a patient-user, through a hollow needle or cannula connected in fluid flow communication with the reservoir. While the threaded channel in the plunger head 134 may be located at the center of the diameter of the plunger head 134, other embodiments may employ a plunger head 134 with an off-center channel (a channel that is laterally spaced relative to the longitudinal axis A of the reservoir). An off-center location of the channel in the plunger head 134 allows the transfer of linear motion (with the rotational motion of the lead shaft 127) to the plunger head 134, while inhibiting rotation of the plunger head 134 relative to the lead shaft 127.

One or more seals 136 may be provided around the outer peripheral surface of the plunger head 134, to inhibit the passage of infusion medium across the plunger head 134, from the medium-retaining interior portion 128 of the reservoir to the external side 129 of the plunger head 134. One or more annular grooves may be provided in the outer peripheral surface of the plunger head 134 for retaining the seal(s) 136. The seal(s) 136 may include one or more o-ring seals or other suitable seal structure and may be made of any suitable seal material, including, but not limited to, rubber, silicone rubber, polyurethane or other plastic material, metal, composite material or the like. The seal(s) 136 may provide sufficient frictional force between the plunger head 134 and the interior surface of the reservoir 126 to inhibit rotation of the plunger head 134 with the rotation of the shaft 127. However, in further embodiments, additional structure may be provided to inhibit rotation of the plunger head with the rotation of the shaft 127, including, but not limited to, one or more projections or shaped portions 138 on the plunger head 134 that fit within corresponding one or more shaped grooves along the length of the interior wall of the reservoir 126, as shown in the cross-section view of FIG. 10 (taken along the cross-section 10-10 of FIG. 9). The shaped projection(s) 138 may have generally curved configurations, with slow curvatures (as compared to an abrupt step), to allow one or more seals 136 to be placed around the plunger head. In alternative embodiments, the interior wall of the reservoir 126 may include a projecting portion extending along the length of the reservoir, for engaging a corresponding groove in the plunger head 134, similar to, but reverse of the projection and groove arrangement shown in FIG. 10. In yet further alternative embodiments, the cross-sectional shape of the plunger head 134 and the reservoir 126 (in the cross-sectional direction shown in FIG. 10) may be non-circular, to inhibit rotation of the plunger head 134 with rotation of the shaft 127. Such non-circular cross-section shapes may include, but are not limited to, an oval or partially oval shape, a polygonal or partially polygonal shape, or the like.

The plunger head 134 includes one or more seals 140 arranged to provide a fluid-tight seal between the plunger head 134 and the lead shaft 127, to inhibit the passage of infusion medium through the central channel of the plunger head 134, from the infusion medium-retaining interior portion 128 of the reservoir to the external side 129 of the plunger head 134, as the plunger head 134 is moved toward the septum end of the reservoir 126. The seal(s) 140 may include an annular structure disposed on one side (such as the infusion-medium-contacting side) of the plunger head 134 and made of any suitable seal material, including, but not limited to, rubber, silicone rubber, polyurethane or other plastic material, metal, composite material or the like. Alternatively, or in addition, the seal(s) 140 may be located within the central channel of the plunger head 134, between the plunger head 134 and the lead shaft 127.

Alternatively, or in addition, the lead shaft 127 may include seal structure to provide or enhance the seal between the plunger head 134 and the lead shaft 127. For example, as shown in FIG. 11, the lead shaft 127 may include one or more seals 142 arranged around the shaft 127, to contact the inner surface of the threaded channel of the plunger head 134. The seal(s) 142 may include a plurality of o-ring seals disposed around the shaft 127 at predetermined intervals along the length of the shaft 127. Alternatively, the seal(s) 142 may include one or more spiral runs of a seal material, spirally wound around the shaft 127. The seal(s) 142 may be made of any suitable seal material, including, but not limited to, rubber, silicone rubber, polyurethane or other plastic material, or the like. The shaft 127 may include one or more annular or spiral grooves in which the seal(s) 142 may reside, to help retain the seal(s) 142 in place on the shaft 127. Alternatively, or in addition, the lead shaft 127 may be coated or wrapped with one or more layers 143 of a seal material, as shown in FIG. 12. The seal material layer 143 may include, but is not limited to rubber, silicone rubber, polyurethane or other plastic material, or other material having suitable elasticity and flexibility to allow the threads of the plunger head 134 to operatively engage the coated or wrapped threads of the lead shaft 127. In yet further embodiments, the inner surface of the central channel in the plunger head may be provided with seals 142 or sealing material 143, in addition to or as an alternative to seals or sealing material on the shaft 127.

The shaft 127 has a connection end 150, for connection to a mating connection end 152 of a drive linkage 154. The drive linkage 154 may be a direct connection to the drive shaft of a motor 144, such that the connection end 152 of the drive linkage 154 rotates with the rotary drive motion of the drive shaft of the motor 144. In other embodiments, the drive linkage 154 may include one or more gears, belts, chains, drive shafts or other linkage structure (not shown) for transferring drive force from a motor 144 to rotational motion of the connection end 152 of the drive linkage. The motor 144 may be any suitable drive device for rotatably driving the connection end 152 of the drive linkage (either directly or through one or more gears, belts, chains, drive shafts or other linkage structure), including, but not limited to the example drive devices described above with respect to the motor 44 in FIG. 4 and escapement wheel arrangements in FIGS. 7a-7d.

The motor 144 and any gears, belts, chains, drive shafts or other linkage structure for coupling the motor 144 to the drive linkage 154 may be contained within the interior of the housing structure of the durable portion 122. The drive linkage or the drive shaft of the motor 144 may extend through an aperture in a wall 160 of the housing structure of the durable portion 122. A seal 162 may be provided within or adjacent the aperture in the wall 160, to inhibit the passage of one or more of moisture, air, biological materials or infusion media into the interior of the housing structure of the durable portion 122. The seal 162 may include, but is not limited to, one or more o-ring seals disposed around the aperture in the wall 160 or around the portion of the drive linkage or drive shaft that extends through the aperture in the wall 160. The seal 162 may be made of any suitable sealing material, including, but not limited to rubber, silicone rubber, polyurethane or other plastic material, metal, composite material or the like.

The connection end 152 of the drive linkage 154 and the connection end 150 of the lead shaft 127 are configured to connect to each other when the durable portion 122 is coupled to the disposable portion 120 and to disconnect from each other when the durable portion 122 is separated from the disposable portion 120. For example, the connection ends 150 and 152 of the lead-shaft 127 and the drive linkage 154, respectively, may include mating features that are configured to easily engage with each other when the connection ends 150 and 152 are brought together and disengage from each other when the connection ends 150 and 152 are moved apart.

In addition, the mating features allow the transfer of rotational motion from the drive linkage 154 to the lead shaft 127, when the connection ends 150 and 152 are engaged.

Figure 13:
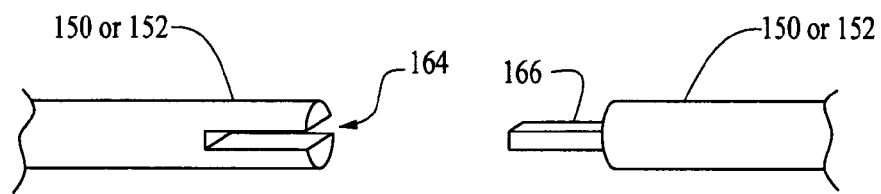
FIG. 13 shows a perspective view of an embodiment of connection ends of the drive linkage and the rotatable shaft of FIGS. 8 and 9.

In one example embodiment as shown in FIG. 13, the mating features may include a slot 164 formed on the connection end 150 of the lead shaft 127 and a tab 166 extending from the connection end 152 of the drive linkage 154, where the tab 166 is shaped to fit within the slot 164 to connect the lead shaft 127 in rotational communication with the drive linkage 154. Alternatively, the slot 164 may be formed on the connection end 152 of the drive linkage 154 and the tab 166 may extend from the connection end 150 of the lead shaft 127. The shape of the tab 166 and the slot 164 in FIG. 13 have a generally rectangular cross-sectional dimension (in the cross-section plane perpendicular to the longitudinal dimension of the lead shaft 127). Other embodiments may employ a tab and slot arrangement with other non-circular cross-sectional shapes (in the cross-section plane perpendicular to the longitudinal dimension of the lead shaft 127) to allow commutation of rotational motion from the drive linkage 154 gto the lead shaft 127. In further alternative embodiments, the mating features may be other shapes that can be readily engaged together to commute rotational motion from the drive linkage to the lead shaft 127 and readily separated to allow the durable portion 122 to be removed from the disposable portion 120 of the delivery device. Such other shapes include, but are not limited to, mating star-shaped structures, cross-shaped structures, non-circular mating shapes (e.g., oval, partially oval, polygonal or partially polygonal), a mating pattern of projections and recesses, or the like, on the connection ends 150 and 152.

In the delivery device embodiments described above, a plunger head 34 or 134 is driven within a reservoir 26 or 126 to drive the infusion medium from the reservoir. Further embodiments of mechanisms for driving a plunger head within a reservoir of a delivery device are described with reference to FIGS. 14-18.

Figures 14, 15:
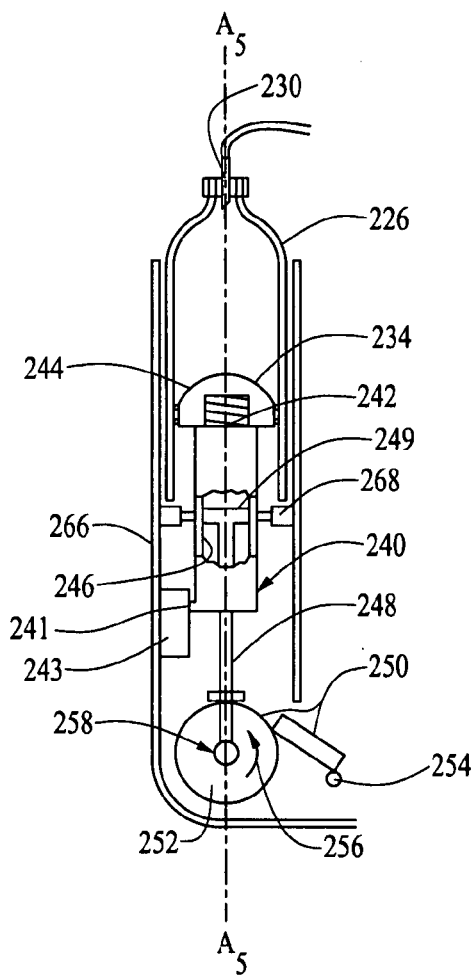
FIGS. 14 and 15 show partial cross-sectional views of reservoirs and drive devices for a delivery device according to further embodiments of the present invention.

In the embodiment of FIG. 14, a reservoir 226 employs a moveable plunger head 234. The reservoir 226 and the plunger head 234 may be similar to the reservoir 126 and plunger head 134 described above with respect to FIG. 9, except that the plunger head 234 need not include a threaded central channel. The plunger head 234 includes seals 236 similar to the seals 136 on the plunger head 134 described above with respect to FIG. 9. The plunger head 234 and reservoir 226 may include further structure to inhibit rotation of the plunger head within the reservoir 226, for example, as described above with respect to example structure for inhibiting rotation of the plunger head 134, including, but not limited to, structure described above with respect to FIG. 10. The reservoir 226 may include a septum 230, similar to the septa 30 and 130 described above. The septum 230 may be used for refilling the reservoir 226 and/or for receiving a hollow needle or cannula to provide a fluid flow path to a patient-user, as described above with respect to the septa 30 and 130.

A slide tube 240 is configured to engage the plunger head 234. The slide tube 240 includes a generally hollow, cylindrical tube made of a suitably rigid material, such as, but not limited to, metal, plastic, ceramic, composite material or the like. One end of the cylindrical slide tube 240 is provided with a mating feature 242 for mating with a corresponding mating feature 244 on the plunger head 234. In the embodiment of FIG. 13, the mating feature 242 includes a projection that extends from the end of the slide tube 240 in the axial direction of the cylindrical shape of the slide tube, while the mating feature 244 includes a recess in the exterior-facing side of the plunger head 234. The recess 244 has a shape adapted to receive the projection 242, when the end of the slide tube 240 is brought into engagement with the exterior-facing side of the plunger head 234. The recess 244 and projection 242 may have corresponding, mating shapes having non-circular cross-sectional dimensions (in the cross-section plane perpendicular to the axis $A_5$) that inhibit relative rotation between the slide tube 240 and the plunger head 234. In another embodiment (as shown in FIG. 15), the plunger head 234 may be connected to (or unitary with) a sleeve 240 that has a hollow interior. The sleeve 240 in FIG. 15 may have a slot-like opening along its longitudinal dimension through which a rotary drive screw 248 may be received. The slot-like opening in the sleeve 240 may be smaller than the diameter of the rotary drive screw 248 and the sleeve 240 may be made of a suitably elastically flexible material to allow the dive screw 248 to be snap fit into the hollow interior of the sleeve 240, through the slot-like opening in the sleeve 240.

The slide tube 240 (in either of the embodiments of FIGS. 14 and 15) has a generally hollow interior and an interior surface 246 that is threaded along at least a portion of its length. The rotary drive screw 248 includes a shaft that extends coaxially with the slide tube 240. The drive screw 248 shaft extends through one end (opposite to the end connected to the plunger head) of the slide tube 240. One end of the drive screw 248 shaft extends into the interior of the slide tube 240 and an opposite end of the drive screw 248 shaft extends outside of the slide tube 240. The drive screw 248 may be threaded along its length (as shown in FIG. 15) or may have a threaded head 249 coupled to the drive screw shaft (as shown in FIG. 14). The threads along the length of the drive screw 248 or the threaded head 249 has threads of a pitch and diameter for engaging and mating with the threads on the threaded interior surface 246 of the slide tube 240. In that arrangement, rotation of the drive screw 248 results in a linear movement of the slide tube 240 along the direction of the axis $A_5$ of the slide tube 240. By rotating the drive screw with a rotary drive device in the appropriate direction, the slide tube pushes the plunger head 234 toward the septum end of the reservoir 226, to force infusion medium through a hollow needle or cannula, to a patient-user.

The end of the drive screw 248 shaft that is external to the slide tube 240 is coupled to a drive device, through suitable drive linkage, to rotate the drive screw 248 in a controlled manner. In the embodiment shown in FIG. 14, the drive device includes a linear actuator 250, such as a piezoelectric actuator device that expands in a linear direction, upon the application of a suitable electrical drive signal. The actuator 250 is arranged to frictionally engage and rotate a rotary wheel 252 a small amount in the direction of arrow 256 with each linear expansion of the actuator 250. The actuator 250 may be selectively controlled to drive the rotary wheel 252 in the direction of arrow 256 for dispensing infusion medium from the reservoir 226, and in the direction opposite to the direction of arrow 256, to retract the plunger head 234 and allow replacement of the reservoir 226. A spring 254 or other suitable structure may be provided to force the actuator 250 against the rotary wheel 252 during expansion of the actuator. The rotational motion of the rotary wheel 252 is transferred to rotational motion of the drive screw 248, through suitable transfer gearing 258. According to the arrangement shown in FIG. 14, the linear actuator 250 may be selectively energized to rotate the wheel 252, which rotates the drive screw 248, which causes the slide tube 240 to move axially and push the plunger head 234 toward the septum end of the reservoir 226, in a controlled, step-like manner.

While FIG. 14 shows a linear drive device that includes a linear actuator for rotatably driving the drive screw 248, other embodiments may employ other drive devices operatively coupled to drive the drive screw 248. For example, FIG. 15 shows an embodiment in which the drive device includes a DC pancake motor 260 that is operatively coupled to the external end of the drive screw 248, through any suitable interface gear arrangement 262. In further embodiments, the drive screw 248 may be operatively coupled to any suitable drive device for rotatably driving the drive screw 248 in a controlled manner, including, but not limited to the example drive devices described above with respect to the motor 44 in FIG. 4 and escapement wheel arrangements in FIGS. 7a-7d.

As shown in FIG. 14, the slide tube 240 may be supported within a portion of a housing structure 266, such as the housing structure of a durable portion of a delivery device. The slide tube 240 extends through an opening in the housing structure 266 to engage the plunger head 234. One or more seals 268 may be disposed around the opening in the housing structure 266 and/or the slide tube 240, to protect the drive device from, for example, moisture, air, biological material or infusion media. The seal(s) 268 may be o-ring seals or other suitable seals made of any suitable seal material, including, but not limited to, the seal materials described above with respect to the seal(s) 45. In addition, an anti-rotation structure may be provided, to inhibit rotation of the slide tube 240 about the axis $A_5$, relative to the housing structure 266. In one embodiment, the anti-rotation structure may include a projection 241 extending from the slide tube 240, for engaging a stop surface 243 that is fixed relative to the housing structure 266. In other embodiments, the seal(s) 268 may provide sufficient frictional engagement with the slide tube and/or the housing structure 266, to inhibit rotation of the slide tube 240 about the axis $A_5$, relative to the housing structure 266.

The reservoir 226 may be located within a disposable housing portion, while the slide tube 240, drive screw 248 and drive device 250 or 260 may be located within a durable housing portion that can selectively couple to or separate from the disposable housing portion, as described above with respect to embodiments of FIGS. 1-13. In a further embodiment, as shown in FIG. 16, a delivery device includes a disposable housing portion 320 having a reservoir retaining portion 324 for containing multiple reservoirs 326 (two in FIG. 16). A piston plunger head 334 is located in each reservoir 326 and may be operated by a slide tube arrangement similar to that shown in either of FIGS. 14 or 15 or other suitable piston moving structure. The delivery device in FIG. 16 includes a durable housing portion 322 for containing one or more drive devices 344 and linkage 362 (which may include, for example bevel gears pinion gears or other suitable gear arrangements) for coupling the drive device(s) to the reservoirs 326. For example, a drive device, slide tube and drive screw arrangement as described with respect to FIGS. 14 and 15 may be included in the durable housing portion 322.

The embodiment of FIG. 17 employs a reservoir 326, plunger head 334, seals 336 and seals 368, similar to the reservoir 226, plunger head 234, seals 236 and seals 268 described above with respect to FIG. 14. The embodiment of FIG. 17 also includes a slide tube 340, similar to the slide tub 240 of FIG. 14, except that the slide tube 340 need not include a threaded interior surface. Instead, the slide tube 340 in FIG. 17 is operatively coupled to a drive device 344 in the form of a linear motor comprising one or more (two in FIG. 17) piezoelectric stacks 346 compressed on a drive shaft 348. The drive shaft 348 may be fixed to a durable portion 366 of delivery device, similar to the durable portion 266 described above.

The linear motor drive device 344 maybe selectively energized by selectively applying electrical control signals to the piezoelectric stacks to cause the slide tube 340 to move toward the septum end of the reservoir 326, to selectively force infusion medium out of the reservoir, as described above with respect to the reservoir 226 in FIG. 14. However, the linear motor drive device 344 of FIG. 17 may be considerably smaller and may consume less power than some of the drive devices and linkages described above for creating rotary motion to drive the slide tube 240 of FIG. 14.

A further embodiment of a delivery device shown in FIG. 18 includes a reservoir 426 and a moveable plunger head 434 within the interior of the reservoir 426. The reservoir 426 and plunger head 434 may be similar to the reservoir 326 and plunger head 334 of FIG. 17, except that the plunger head 434 need not have a mating feature for engaging a slide tube. Instead, the plunger head 434 is configured to abut an expandable bellows 436 and move along the direction of the longitudinal axis $A_6$ of the reservoir 426 with the expansion of the bellows 436.

The bellows 436 is any suitable expandable structure that includes an interior volume that is expandable and that is capable of containing a hydraulic fluid. The delivery device in FIG. 18 includes a second reservoir 438 for containing hydraulic fluid, a conduit or tube 440 connected to the hydraulic fluid reservoir 438 and the bellows 436, for providing a fluid-flow communication path between the hydraulic fluid reservoir 438 and the interior volume of the bellows 436. A pumping mechanism 444 is provided to selectively pump hydraulic fluid into the bellows 436.

In the embodiment shown in FIG. 18, the pumping mechanism 444 is a peristaltic pump device including a rotor 446 mounted for rotation about an axis R. The rotor 446 has a plurality of rollers or pads arranged to engage a portion of the conduit 440 and roll or slide along a length of the conduit 440. The conduit 440 may be elastically flexible, at least along the length engaged by the rotor 446 rollers or pads. The length of the conduit 440 engaged by the rotor 446 may be arranged along an arcuate surface 448, where the arc of the surface 448 corresponds to the diameter of the rotor 446. The arcuate surface 448 may be a surface of a wall or other structure formed within the durable housing portion 422.

By rolling across the conduit 440 on the arcuate surface 448, the rotor rollers or pads may engage and squeeze the conduit 440 during the period of motion of the rollers or pads along the length of the arcuate surface 448. The rolling or sliding motion of the rotor rollers or pads along the arcuate length of the flexible conduit 440 creates a sufficient pressure differential to drive hydraulic fluid from the hydraulic fluid reservoir 438 to the interior of the bellows 436, in a manner controlled by the controllable rotary motion of the rotor 444. Any suitable rotary drive device or arrangement, such as, but not limited to those described herein, may be employed to drive the rotor 444 in a controlled manner.

As hydraulic fluid is pumped into the bellows 436 by the pumping mechanism 442, the hydraulic fluid creates a fluid pressure within the bellows sufficient to cause the bellows to expand an amount dependent upon the amount of hydraulic fluid pumped into the bellows. As the bellows 436 expands, the end of the bellows that abuts the plunger head 434 is moved toward the septum end of the reservoir 426 and pushes the plunger head 434 toward the septum end of the reservoir 426. As the plunger head 434 is moved toward the septum end of the reservoir 426, the plunger head forces infusion medium within the reservoir 426 out through a suitable hollow needle or cannula, to a patient-user.

While the embodiment of FIG. 18 employs a peristaltic pump device 444 to drive hydraulic fluid from the hydraulic fluid reservoir 438 to the bellows 436 in a controlled manner, other embodiments may employ other suitable pump devices for performing that function, including, but not limited to, conventional piston pumps, impeller pumps, membrane pumps, or the like.

In the embodiment shown in FIG. 18 the reservoir 426 may be located in a disposable portion 420 of the delivery device, while the hydraulic fluid reservoir 438, hydraulic fluid pump device 444, pump drive motor (not shown) and bellows 436 may be located in a durable portion 422 of the delivery device. The disposable portion 420 and durable portion 422 may be configured to be coupled together for operation, or separated for servicing, as described above with respect to disposable portion 20 and durable portion 22 in FIGS. 2 and 3. The disposable portion 420 may be provided with a needle insertion mechanism, for inserting a hollow needle or cannula into a patient-user's skin and connecting the hollow needle or cannula in fluid flow communication with the interior of the reservoir 426, when the disposable portion 420 is secured to a patient-user's skin, as described above with respect to the disposable portion 20 of FIGS. 2 and 3. Examples of mechanisms that may be used for inserting a hollow needle or cannula into a patient-user and coupling the needle and cannula in fluid flow communication with a reservoir are described in U.S. patent application Ser. No. 11/211,095, filed Aug. 23, 2005, and U.S. Patent Application Ser. No. 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006.

Figure 19:
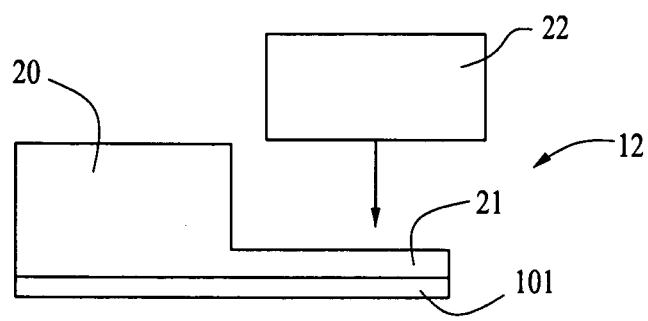
FIG. 19 shows a schematic side view of an arrangement of a durable housing portion and a disposable housing portion of a delivery system according to an embodiment of the invention consistent with the embodiment of FIG. 3.

In embodiments described above, the disposable housing portion (e.g., 20 in FIG. 3) is provided with a base portion 21 that may be secured to the patient-user's skin by, for example, but not limited to, an adhesive material provided on the bottom surface of the base portion 21. That arrangement is generally represented, in side view, in FIG. 19, wherein an adhesive material 101 is provided on the bottom surface (skin-facing surface) of the base 21 of the disposable housing portion 20. As shown in FIGS. 2, 3 and 19, the durable housing portion 22 may be configure to be arranged on the base 21 of the disposable housing portion 20 to engage and connect to the disposable housing portion 22. In such an arrangement, the base 21 may be disposed between the durable housing portion 22 and the patient-user's skin, during operation, such that only the base 21 of the disposable housing portion remains in contact with the patient-user's skin, during operation.

Figure 20:
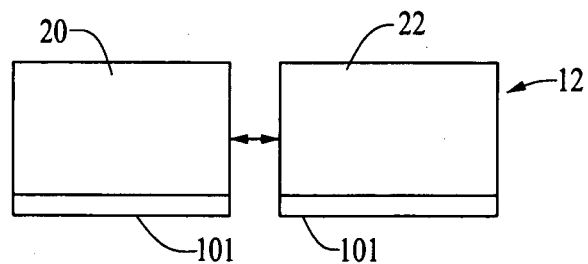
FIG. 20 shows a schematic side view of an arrangement of a durable housing portion and a disposable housing portion of a delivery system according to another embodiment of the invention.

However, in other embodiments, the durable housing portion 22 and the disposable housing portion 20 may be configured to engage each other in a side-by-side arrangement, for example, as represented in FIG. 20. In the side-by-side arrangement in FIG. 20, either one or both of the durable housing portion 22 and the disposable housing portion 20 may be provided with a base having an adhesive material 101 (and a peelable cover layer 23 as shown in FIG. 3).

Figure 21:
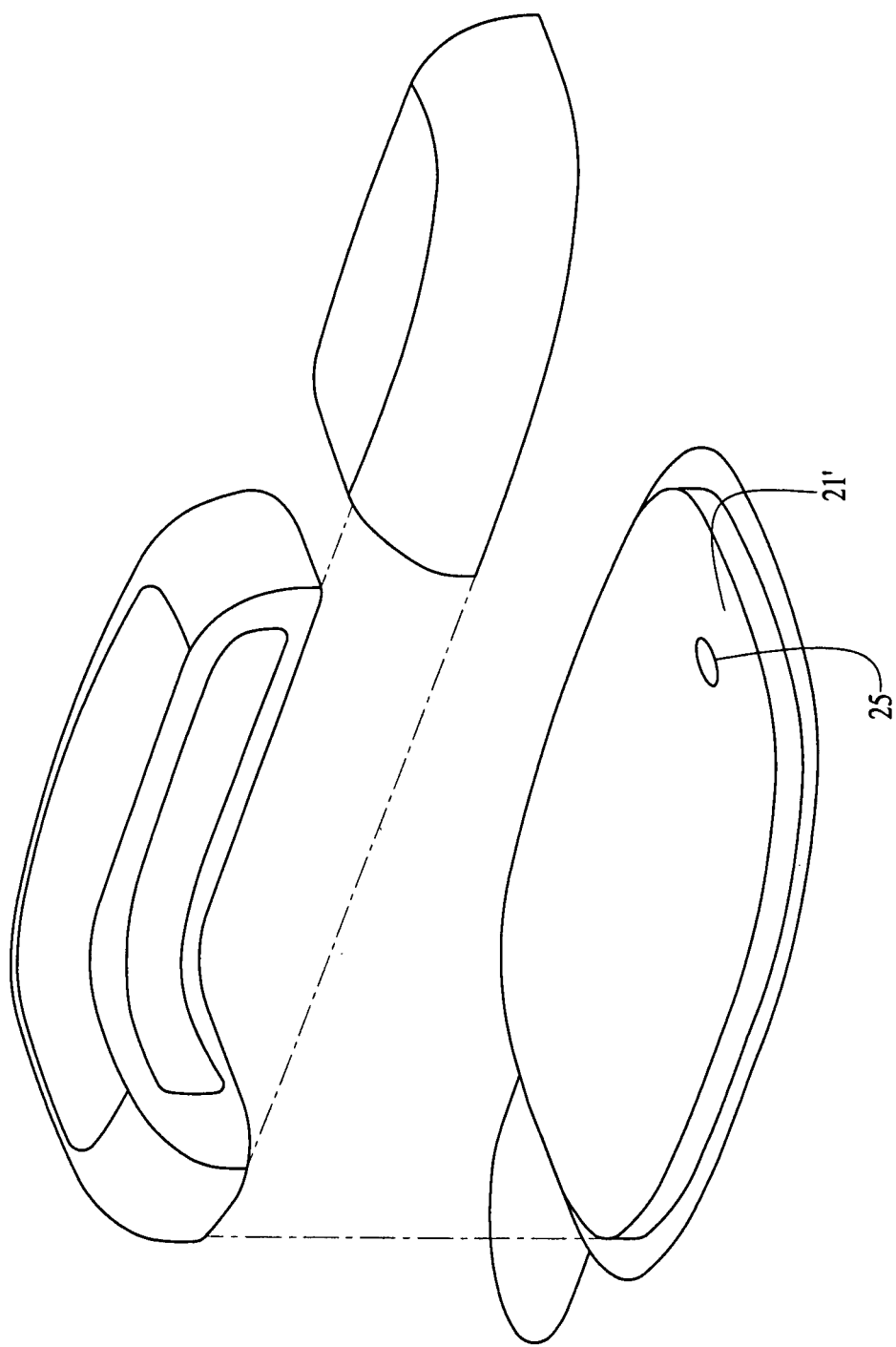
FIG. 21 shows a partially exploded view of a delivery device according to an embodiment of the invention.

In yet further embodiments, as represented by FIG. 21, one or both of the durable housing portion 22 nd the disposable housing portion 20 may be attachable and detachable from a separate base member 21'. Suitable connecting structure, such as described above for connecting the durable housing portion and the disposable housing portion together, may be employed for connecting the durable housing portion and the disposable housing portion to the base member 21'. The separate base member 21' may include a generally flat, plate-like structure made of any suitably rigid material including, but not limited to, plastic, metal, ceramic, composite material or the like. The base member 21' has a surface (the upper-facing surface in FIG. 21) to which the disposable housing portion 20 and the durable housing portion 22 may be attached. The base member 21' has a second surface (the lower-facing surface in FIG. 21) to which an adhesive material and a peelable cover film may be applied, as described above, to allow the base member 21' to be secured to a patient-user's skin.

The base member 21' may include a needle inserter device 25, as described above. Examples of suitable needle inserter devices are described in U.S. patent application Ser. No. 11/211,095, filed Aug. 23, 2005, and U.S. Patent Application Ser. No 60/839,840, titled INFUSION MEDIUM DELIVERY SYSTEM, DEVICE AND METHOD WITH NEEDLE INSERTER AND NEEDLE INSERT DEVICE AND METHOD, filed Aug. 23, 2006, each of which is incorporated herein by reference in its entirety. In such embodiments, the base member 21' may be secured to a patient-user's skin. Then, the needle inserter 25 may be activated to insert a hollow needle or cannula into the patient-user's skin. Then, after the hollow needle or cannula is inserted, the durable housing portion 22 and the disposable housing portion 20 may be attached to the base member 21', to connect the reservoir within the disposable housing portion 20 in fluid flow communication with the hollow needle or cannula. In one embodiment, the durable housing portion 22 and the disposable housing portion 20 may be connected together (for example, in the manner described above) before attaching those housing portions to the base member 21'. In a further embodiment, one of the durable and disposable housing portion is attached to the base member 21' before the durable and disposable housing portions are connected together. In such further embodiment, the needle inserter device may be activated to insert a hollow needle or cannula into the patient-user's skin after the disposable housing portion is attached to the base member 21' (either before or after the durable and disposable housing portions are connected together).

Alternatively, reference number 25 may represent an opening in the base member 21' that aligns with a needle inserter device (or aligns with a further opening) located in the disposable housing portion 20, when the disposable housing portion 20 is attached to the base member 21'. In such embodiments, the base member 21' may be secured to the patient-user's skin. Then the disposable housing portion 20 is attached to the base member 21' (either before or after the durable and disposable housing portions are connected together). Once the disposable housing portion 20 is attached to the base member 21', the needle inserter device 25 may be activated to insert a hollow needle or cannula into a patient-user's skin (either before or after the durable and disposable housing portions are connected together).

Figure 22:
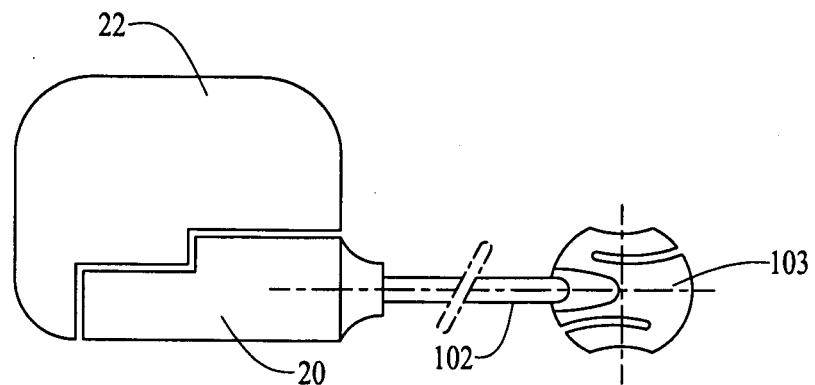
FIG. 22 shows a schematic top view of an arrangement of a durable housing portion and a disposable housing portion of a delivery system according to an embodiment of the invention.

Also, while embodiments described above may include an on-board needle or cannula injector device that may be activated through the operator or opening 25, other embodiments may employ an injection site module 103 that is external to the disposable housing portion 20, but connected to the disposable housing portion 20, through a suitable conduit 102, as shown in FIG. 22. The external injection site module 103 may include a needle or cannula injector device structure and an operator or opening (similar to the operator or opening 25 described above) through which the injector device may be activated. Alternatively or in addition, the external injection site module 103 may include an infusion set such as, but not limited to an infusion set as described or referenced in U.S.

patent application Ser. No. 10/705,686, filed Nov. 10, 2003, titled "Subcutaneous Infusion Set" (Publication No. 2005/0101910) and/or U.S. patent application Ser. No. 11/004,594, filed Dec. 3, 2004, titled "Multi-Position Infusion Set Device And Process" (Publication No. 2006/0129090), each of which is assigned to the assignee of the present invention and each of which is incorporated herein by reference, in its entirety.

The conduit 102 that connects the module 103 with the disposable housing portion 20 may be any suitable tubing structure having a fluid flow passage, such as, but not limited to, a flexible tube made of plastic, silicone or the like. An adhesive material may be provided on the tubing structure (or between the tubing structure and the patient-user's skin) to secure the tubing to the patient-user's skin. By locating the injection site module 103 external to the disposable housing portion 20, the disposable housing portion 20 and the durable housing portion 22 may be clipped to a patient-user's clothing, belt, suspender or other article of apparel or may be held in a pocket of an article of apparel or carried in a purse or the like.

In one embodiment, the conduit 102 may be fixed at one end to the disposable housing portion 20, in fluid-flow communication with the reservoir within the disposable housing portion 20, and fixed at a second end to an external injection site module 103, for connection in fluid-flow communication with a hollow needle or cannula, as described above. In further embodiments, one or both of the ends of the conduit 102 may include suitable connection structures that allow the conduit ends to be selectively connected in fluid-flow communication with, and selectively disconnected from the disposable housing portion 20 and/or the injection site module 103. Such connectors may comprise a hollow needle and septum, a Luer connector, or other suitable fluid-communication connectors. In such embodiments, the disposable housing portion 20 and the durable housing portion 22 may be disconnected from the module 103, for example, by disconnecting one of the ends of the conduit 102 from the module 103 or the disposable housing portion 20, while leaving the module 103 in place (without requiring the patient-user to withdraw the needle or cannula and, later, insert a needle or cannula to resume operation). In this manner, a patient-user may readily disconnect and remove the disposable housing portion 20 and durable housing portion 22, for example, to allow the patient-user to shower, bath, swim or conduct other activities, yet also allow the patient-user to readily re-connect the disposable housing portion 20 to the module 103, for example, upon completion of such activities.

Figure 23:
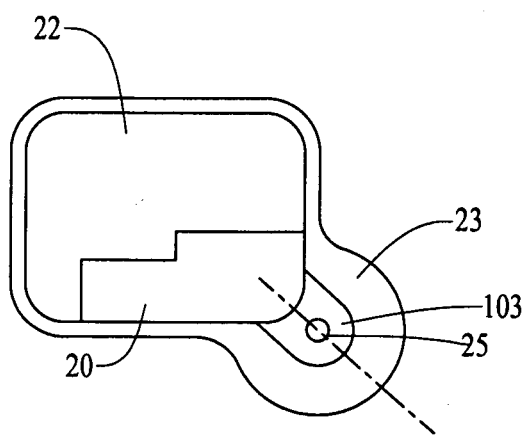
FIG. 23 shows a schematic top view of an arrangement of a durable housing portion and a disposable housing portion of a delivery system according to another embodiment of the invention.

In yet further embodiments, the conduit 102 may be eliminated and an injection site module 103 may be directly connected with the disposable housing portion 20, as shown in FIG. 23. In such an embodiment, one or more suitable fluid flow passages are provided through the disposable housing portion 20 and into the injection site module 103, for fluid-flow communication between the reservoir in the disposable housing portion 20 and a hollow needle or cannula, as described above. Also, in such embodiments, the injection site module 103 and the disposable housing portion 20 may include mating connection structures to allow the injection site module 103 and the disposable housing portion 20 to be selectively connected and disconnected from each other.

Figure 24:
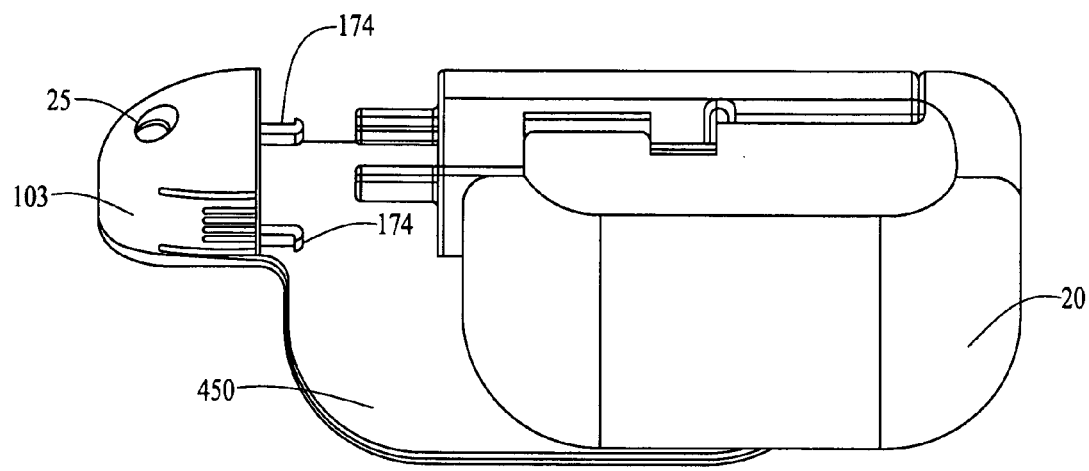
FIGS. 24 and 25 show a perspective view of a connection arrangement for a disposable housing portion and an injection site module.
Figure 25:
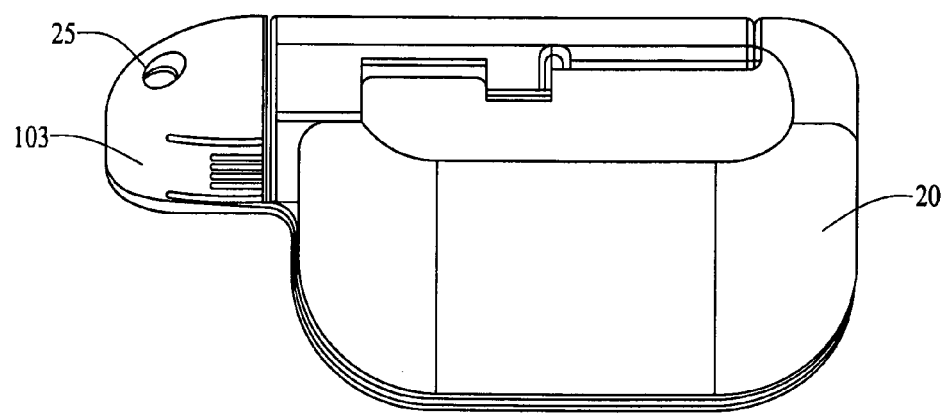

Various examples of mating arrangements, for directly connecting an injection site module 103 to a disposable housing portion are described with reference to FIGS. 24-29. FIGS. 24 and 25 show an example arrangement, in which an injection site module 103 includes at least one (two in FIG. 23) protruding engagement pawl 174 that are configured to be received in a corresponding number of receptacles on the disposable housing portion 20 (similar to the pawls 74 and receptacles 76 described in U.S. Patent Application Ser. No. 60/839,741, titled INFUSION PUMPS AND METHODS AND DELIVERY DEVICES AND METHODS WITH SAME, filed Aug. 23, 2006, which has been incorporated herein by reference. In other embodiments, the pawl(s) 174 may be located on the disposable housing portion 20, while the corresponding receptacles may be located on the module 103. In yet other embodiments, each of the disposable housing portion 20 and the module 103 may include one or more pawls and one or more receptacles.

The pawls 174 and receptacles may be configured to allow a patient-user to manually slide the pawls into the receptacles as the disposable housing portion 20 and the module 103 are brought together. When the pawls 174 are received in the corresponding receptacles, the module 103 is secured to the disposable housing portion 20. The pawls 174 may include a shaped portion or head to provide a snap-fit with the receptacles, when the pawls 174 are fully received within the receptacles. The pawls 174 may be configured with sufficient flexibility to allow the patient-user to separate the disposable housing portion 20 from the module 103, by applying a sufficient force to full those two parts away from each other and unsnap the pawls 174 from the receptacles. In the embodiment of FIGS. 23 and 24, the module 103 may be attached to or may include a base portion 450 that may be secured to a patient-user's skin during operation, in lieu of the extended base 21 of the disposable housing portion 20 described above. The base portion 450 may include an adhesive material as described above with respect to the base 21 of the disposable housing portion 20.

Figure 26:
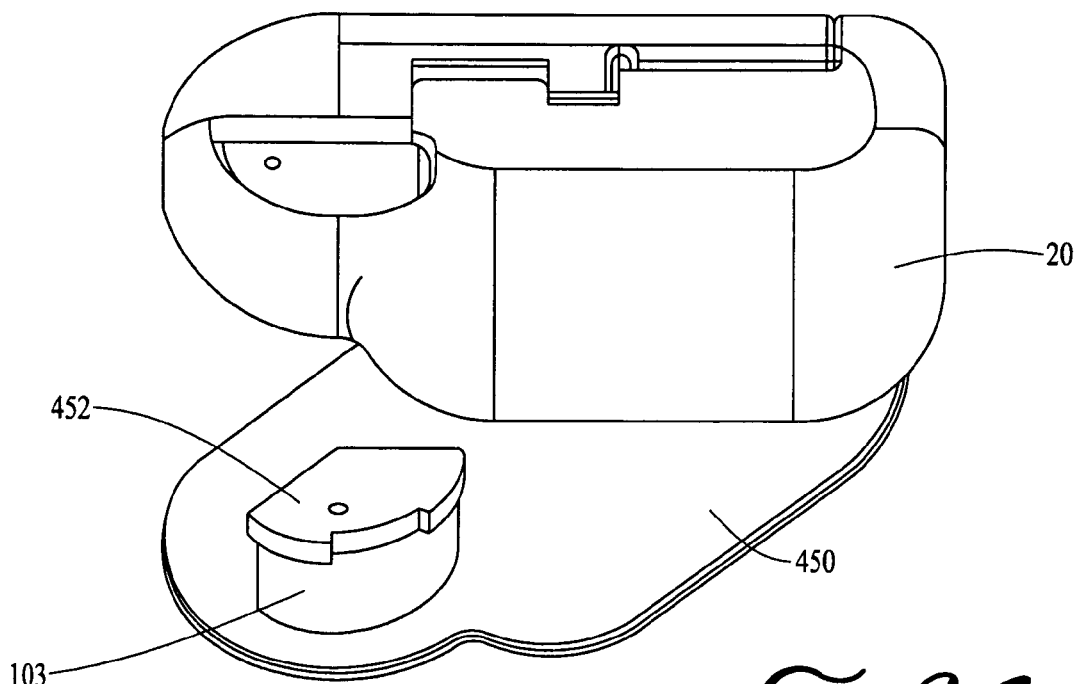
FIGS. 26 and 27 show a perspective view of another connection arrangement for a disposable housing portion and an injection site module.
Figure 27:
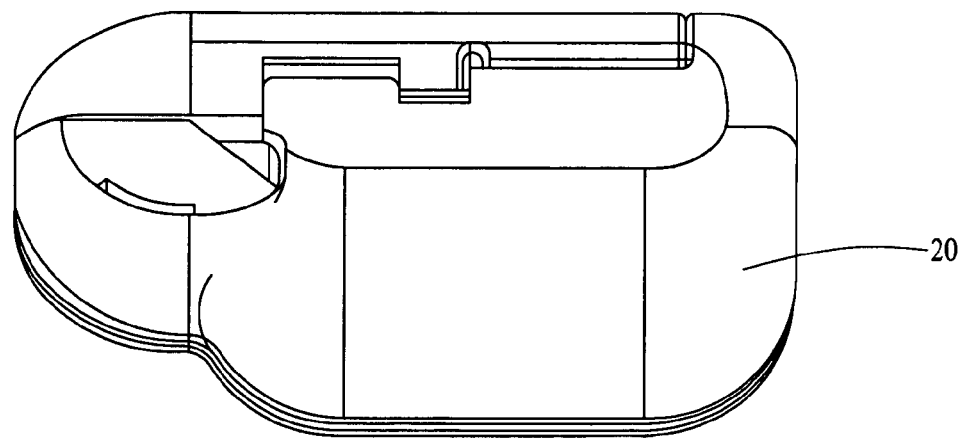

Another example of a connection structure is described with reference to FIGS. 26 and 27, wherein the module 103 includes a shaped head 452 configured to be received within a correspondingly shaped opening or receptacle in the disposable housing portion 20. The shaped head 452 may be configured with a shape that allows the head to be received in the receptacle when the disposable housing portion 20 is aligned relative to the module 103 in a first alignment position, as shown in FIG. 26, and further allows the disposable housing portion 20 to be rotated relative to the module 103 while the head 452 is received within the receptacle to a second alignment position as shown in FIG. 27. The receptacle in the disposable housing portion 20 may be shaped to allow the head 452 to be freely received or removed from the receptacle, when the disposable housing portion 20 is in the first alignment position (FIG. 26), yet abut the head 452 and inhibit separation of the head 452 from the receptacle (and, thus, inhibit separation of the disposable housing portion 20 from the module 103), when the disposable housing portion is in the second alignment position (FIG. 27).

Figure 28:
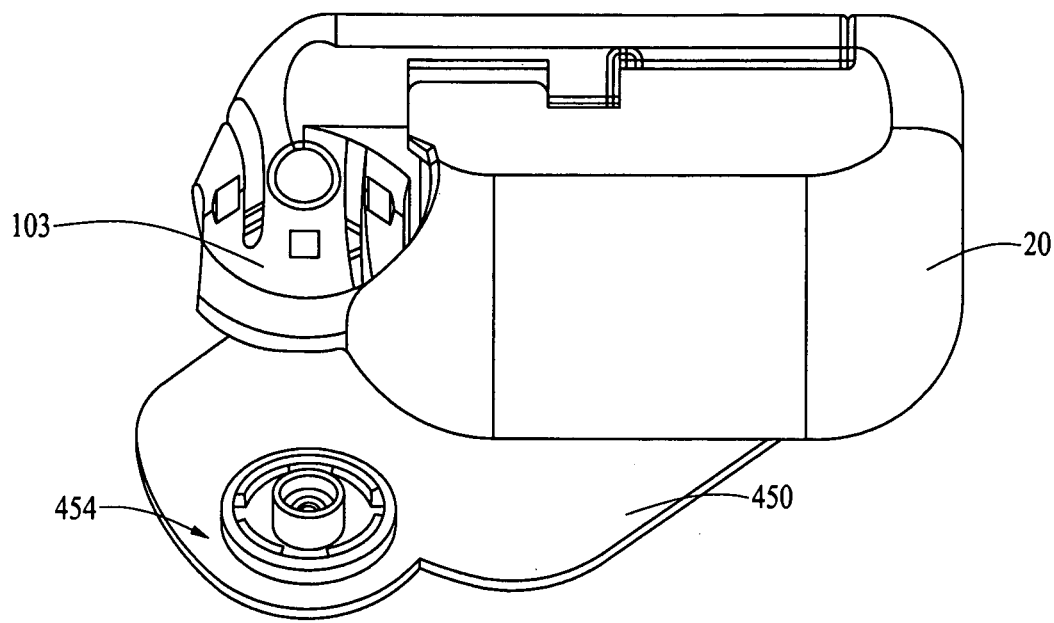
FIGS. 28 and 29 show a perspective view of yet another connection arrangement for a disposable housing portion and an injection site module.
Figure 29:
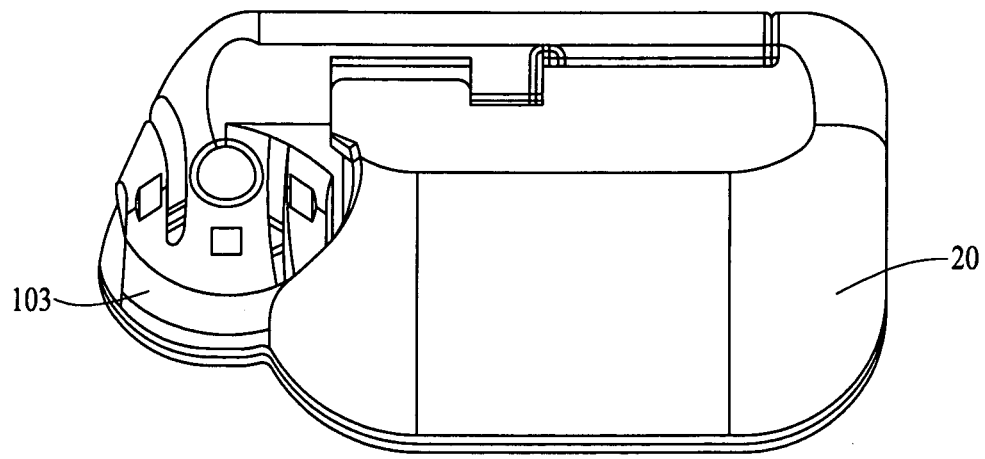

A further example of a connection structure is described with reference to FIGS. 28 and 29, wherein the module 103 includes a shaped receptacle 454 configured to receive a correspondingly shaped connector member in the disposable housing portion 20. The shaped receptacle 454 may be configured with a shape that allows the connector member of the disposable housing portion to be engaged with the receptacle 454 when the disposable housing portion 20 is aligned relative to the module 103 in a first alignment position, as shown in FIG. 28, and further allows the disposable housing portion 20 to be rotated relative to the module 103, while the receptacle 454 is engaged within the connector member, to a second alignment position as shown in FIG. 28. The receptacle 454 and the connector member in the disposable housing portion 20 may be shaped to allow the connector member to be freely engage the receptacle 454, when the disposable housing portion 20 is in the first alignment position (FIG. 28), yet lock with the receptacle 454 and inhibit separation of the connector member from the receptacle (and, thus, inhibit separation of the disposable housing portion 20 from the module 103), when the disposable housing portion is in the second alignment position (FIG. 29). The receptacle 454 and connection member may include any suitable known rotary connection structures for connecting two structures together upon engagement and relative rotation of the two structures in one direction, yet allow the two structures to be disengaged and separated from an engaged arrangement, by relative rotation of the two structures in the second, opposite direction.

In yet further embodiments, the injection site module may be formed as a unitary structure with the disposable housing portion 20. Also, in any of the embodiments described above, one or more sensors may be located in the disposable housing portion 20, the injection site module 103 or the durable housing portion 22, for sensing a biological condition, including, but not limited to, blood glucose level, level of infusion medium in the patient-user's blood and/or other conditions. Such sensor(s) may include a hollow needle or cannula and/or a set of micro-needles, as described above, for piercing the patient-user's skin to convey fluid from the patient to the sensor.

Various aspects of the multiple embodiments described above may be employed independently or in combinations thereof. Significant advantages can be obtained from various embodiments and combinations described herein, wherein an at-site delivery system may be made of two parts, including a disposable portion and a non-disposable portion. The disposable portion may contain all materials that are in direct contact with the infusion medium, such as reservoir body, reservoir piston, septum systems and injection needle. The non-disposable portion could contain substantially the materials that are not in contact with the medication including the drive system, pressure or force sensing system, battery, electronics, display, and non-disposable housing. The pump could be designed such that the disposable portion (user filled or pre-filled cartridge) is inserted into the non-disposable portion. By simplifying the manner in which the disposable portion of the delivery device can be replaced and by simplifying the manner in which the delivery device can be re-activated after replacing a disposable portion, a greater number of patient-users will be able to use and benefit from such delivery devices.

While particular embodiments of the present invention have been shown and described, it will be obvious to those skilled in the art that the invention is not limited to the particular embodiments shown and described and that changes and modifications may be made without departing from the spirit and scope of the claimed invention. For example, while embodiments described above may include an adhesive material and a cover film 23 (FIGS. 2 and 3), further embodiments may include a plurality of adhesive material layers alternating with a corresponding plurality of cover film layers 23, to allow the delivery device to be secured, removed and re-secured to the patient-user's skin one or more times.

In such embodiments, a first cover film layer located at the end of the stack of alternating layers of adhesive material and cover film, may be removed to expose a first layer of adhesive material. With the first layer of adhesive material exposed, the delivery device (or component thereof) may be adhered to a patient-user's skin, as described above. After a suitable period of usage, the delivery device (or component having the adhesive) may be removed from the patient-user's skin, for example, for servicing, re-filling, replacement of one or more components, or the like. After removal of the delivery device (or component) from the patient-user's skin, a second cover film layer on the delivery device (or component) may be removed to expose a second layer of adhesive material. With the second layer of adhesive material exposed, the delivery device (or component) may be secured to the same patient-user or, in certain contexts, to a different patient-user, for further operation. The process may be repeated a number of times up to the number of adhesive material and cover film layer pairs are included in the plural alternating layers of adhesive material and cover film.

In addition, while embodiments described above include an injection site located on the disposable housing portion 20 or in an external injection site module 103, other embodiments may employ an injection site located in the durable housing portion 22 and connected, through suitable fluid-flow passages, to the reservoir in the disposable housing portion 20, when the durable housing portion and disposable housing portion are engaged. Also, while embodiments are described above in the context of delivery devices for delivering an infusion medium from a reservoir to a patient-user, other embodiments may be operated to withdraw a fluidic medium from a patient-user (or other source) and transfer the fluidic medium to the reservoir. Such other embodiments may be operated by operating the drive device to selectively move the piston plunger away from the septum-end of the reservoir (to increase the fluid-retaining volume of the reservoir) to create a negative pressure sufficient to draw fluid from the patient-user (or other source) to which the hollow needle or cannula is secured.

What is claimed is:

1. A delivery device for delivering an infusion medium to a user, the device comprising:
   a disposable housing adapted to be carried by a user, the disposable housing including a reservoir container retaining portion;
   a durable housing configured to be selectively engaged with and disengaged from the disposable housing to allow disposal of the disposable housing without disposing of the durable housing, the durable housing having an enclosure structure that separates an enclosed interior volume from an exterior volume located external to the enclosure structure;
   a reservoir comprising a container having an interior for containing a fluidic medium and a piston plunger moveable within the interior of the reservoir container in a direction of an axis of the reservoir container, wherein the reservoir container is supported and carried by the disposable housing, the reservoir container being configured to be received by the reservoir container retaining portion and to be manually removable from the reservoir container retaining portion once received by the reservoir container retaining portion;
   a lead shaft supported for rotation about a lead shaft axis and carried by the durable housing, the lead shaft having a threaded portion located in the exterior volume, external to the enclosed interior volume of the durable housing, the threaded portion of the lead shaft being arranged to engage the piston plunger at an engagement location on the piston plunger and move the piston plunger along the axis of the reservoir with rotation of the lead shaft when the durable housing is engaged with the disposable housing, the lead shaft axis being laterally offset from the axis of the reservoir at the engagement location, the lead shaft having a connection portion located within the enclosed interior volume of the durable housing, wherein the lead shaft extends through an aperture in the durable housing between the interior volume of the durable housing and the exterior volume; and a drive device operatively connected to the connection portion of the lead shaft, to selectively rotate the lead shaft.

2. A delivery device according to claim 1, further comprising a seal adjacent to the aperture in the durable housing, to seal the aperture through which the lead shaft extends.

3. A delivery device according to claim 1, further comprising electrical control circuitry contained in the durable housing, wherein the electrical control circuitry controls the delivery of infusion medium from the reservoir container to the user when the durable housing and the disposable housing are engaged.

4. A delivery device according to claim 1, wherein the disposable housing comprises a base portion having a bottom surface and an adhesive material on the bottom surface for securing the disposable housing to the skin of the user.

5. A delivery device according to claim 1, wherein the reservoir includes a septum that may be pierced by a hollow needle for providing a fluid flow path from the interior of the reservoir container to the hollow needle.

6. A delivery device according to claim 1, wherein the piston plunger comprises a plunger head disposed within the interior of the reservoir container, an engagement portion located outside of the reservoir container for engaging the threaded portion of the lead shaft when the durable housing and the disposable housing are engaged, and a piston shaft extending from the plunger head to the engagement portion.

7. A delivery device according to claim 6, wherein the engagement portion of the piston plunger comprises a threaded surface having threads configured to operatively engage threads on the threaded portion of the lead shaft when the durable housing and the disposable housing are engaged.

8. A delivery device according to claim 7, wherein the lead shaft has a longitudinal axis, and wherein the threaded surface of the engagement portion of the piston plunger is curved at least partially around the longitudinal axis of the lead shaft, upon the engagement portion of the piston plunger being operatively engaged with the lead shaft.

9. A delivery device according to claim 6, wherein the plunger head disposed within the interior of the reservoir container has an outer peripheral surface and at least one seal arranged around the outer peripheral surface, for sealing the interior of the reservoir container.

10. A delivery device according to claim 1, wherein the piston plunger comprises a plunger head disposed within the interior of the reservoir container, the plunger head having an outer peripheral surface and at least one seal arranged around the outer peripheral surface, for sealing the interior of the reservoir container.

11. A delivery device according to claim 1, wherein the drive device is located within the enclosed interior volume of the durable housing.

12. A delivery device according to claim 1, further comprising an anti-rotation structure to inhibit the piston plunger from rotating within the reservoir container.

13. A delivery device according to claim 12, wherein the reservoir container has an interior surface and wherein the anti-rotation structure comprises at least one projection extending from one of the piston plunger and the interior surface of the reservoir container and at least one channel provided in the other one of the piston plunger and the interior surface of the reservoir container, wherein the at least one projection is configured to extend at least partially into the at least one channel.

14. A delivery device according to claim 1, wherein:
the piston plunger comprises a plunger head disposed within the interior of the reservoir container, and a piston shaft coupled to the plunger head, the piston shaft having a longitudinal axis and a threaded portion extending along the longitudinal axis at least partially outside of the reservoir container; and
the threaded portion of the lead shaft comprises a threaded head arranged to engage the threaded portion of the piston shaft, when the durable housing and the disposable housing are engaged.

15. A delivery device according to claim 1, wherein the drive device comprises:
an escapement wheel supported for rotation, the escapement wheel having a plurality of teeth, the escapement wheel being operatively connected to rotate the lead shaft with rotation of the escapement wheel;
a drive pawl supported for linear movement between a start position and an end position and having a drive surface arranged to engage a tooth of the escapement wheel and rotate the escapement wheel in a first direction as the drive pawl moves between the start and end positions; and
an actuator operatively connected to the drive pawl, for selectively moving the drive pawl from the start position to the end position.

16. A delivery device according to claim 1, wherein the drive device comprises:
a drive wheel supported for rotation, the drive wheel having a plurality of teeth, the drive wheel being operatively connected to rotate the lead shaft with rotation of the drive wheel;
an escapement wheel supported for rotation and having one or more teeth for engaging one or more corresponding teeth on the drive wheel and rotating the drive wheel less than 360 degrees for each 360 degree rotation of the escapement wheel; and
a drive motor coupled to the escapement wheel to selectively rotate the escapement wheel.

17. A device according to claim 1, wherein the lead shaft has two ends and, when the durable housing portion is in engagement with the disposable housing portion, the engagement location of the piston plunger is engaged by the lead shaft at a portion of the lead shaft that is between and spaced from both ends of the lead shaft.

18. A device according to claim 1, wherein the lead shaft has two ends and, when the durable housing portion is engagement with the disposable housing portion, both ends of the lead shaft are free of engagement with the piston plunger, while the engagement location of the piston plunger is engaged by the lead shaft at a portion of the lead shaft that is between and spaced from both ends of the lead shaft.

19. A device according to claim 1, wherein the reservoir container interior has a generally cylindrical shape through which a central axis of the generally cylindrical shape extends, and wherein the axis of the reservoir container comprises the central axis of the generally cylindrical shape of the reservoir container interior.

20. A device according to claim 1, wherein the reservoir container interior has a lengthwise dimension that is longer than its lateral dimension and wherein the axis of the reservoir container extends through the reservoir container interior in the lengthwise dimension of the reservoir container interior.

21. A delivery device according to claim 1, wherein the disposable housing comprises a base portion having a bottom surface configured to be secured to a user and to remain secured to the user when the reservoir container is received within the reservoir container retaining portion and when the reservoir container is manually removed from the reservoir container retaining portion, and further to remain secured to the user when the durable housing is engaged with and disengaged from the disposable housing.

22. A delivery device according to claim 1, wherein the disposable housing comprises a base portion having a bottom surface configured to be secured to a user, the base portion further having a top surface on which the reservoir container retaining portion is disposed in an orientation to retain the reservoir container in a position at which the engagement location of the piston plunger engages with the lead shaft when the durable housing is engaged with the disposable housing and disengages from the lead shaft when the durable housing is disengaged from the disposable housing.

23. A delivery device according to claim 22, wherein the bottom surface of the base portion of the disposable housing is configured to remain secured to the user when the reservoir container is received within the reservoir container retaining portion and when the reservoir container is manually removed from the reservoir container retaining portion, and further to remain secured to the user when the durable housing is engaged with and disengaged from the disposable housing.

24. A delivery device according to claim 1, wherein the reservoir container retaining portion comprises a housing having an interior volume and a port that is open to the interior volume, the port and interior volume of the reservoir container retaining portion housing being configured to receive the reservoir container through the port and at least partially into the interior volume, wherein the reservoir container and the reservoir container retaining portion housing are configured to inhibit rotation of the reservoir container relative to the reservoir container retaining portion housing once the reservoir container is received within the interior volume of the reservoir container retaining portion housing.

25. A method of assembling a delivery device for delivering an infusion medium to a user, the method comprising:
providing a disposable housing adapted to be carried by a user, the disposable housing including a reservoir container retaining portion;
configuring a durable housing to be selectively engaged with and disengaged from the disposable housing to allow disposal of the disposable housing without disposing of the durable housing, the durable housing having an enclosure structure that separates an enclosed interior volume from an exterior volume located external to the enclosure structure;
receiving and carrying a reservoir container by the reservoir retaining portion of the disposable housing, the reservoir container having an interior for containing a fluidic medium, the reservoir container being configured to be manually removable from the reservoir container retaining portion once the reservoir container is received by the reservoir container retaining portion;
supporting a piston plunger for movement within the interior of the reservoir container in a direction of an axis of the reservoir container;
supporting and carrying a lead shaft by the durable housing for rotation about a lead shaft axis, including arranging a threaded portion of the lead shaft external to the enclosed interior volume of the durable housing, arranging a connection portion of the lead shaft within the enclosed interior volume of the durable housing, and extending the lead shaft through an aperture in the durable housing between the interior volume of the durable housing and the exterior volume;
engaging the threaded portion of the lead shaft with the piston plunger at an engagement location on the piston plunger for moving the piston plunger along the axis of the reservoir with rotation of the lead shaft when the durable housing is engaged with the disposable housing, the lead shaft axis being laterally offset from the axis of the reservoir at the engagement location; and
operatively connecting a drive device to the connection portion of the lead shaft, to selectively rotate the lead shaft.

26. A method according to claim 25, further comprising locating a seal adjacent to the aperture in the durable housing, to seal the aperture through which the lead shaft extends.

27. A method according to claim 25, further comprising supporting electrical control circuitry in the durable housing, wherein the electrical control circuitry controls the delivery of infusion medium from the reservoir to the user when the durable housing and the disposable housing are engaged.

28. A method according to claim 25, further comprising providing an anti-rotation structure to inhibit the piston plunger from rotating within the reservoir container.

29. A device for conveying a fluidic medium to or from a user, the device comprising:
a first housing adapted to be carried by a user, the first housing including a reservoir container retaining portion;
a second housing configured to be selectively engaged with and disengaged from the first housing, the second housing having an enclosure structure that separates an enclosed interior volume from an exterior volume located external to the enclosure structure;
a reservoir comprising a container having an interior for containing a fluidic medium and a piston plunger moveable within the interior of the reservoir container in a direction of an axis of the reservoir container, wherein the reservoir container is supported and carried by the first housing, the reservoir container being configured to be received by the reservoir container retaining portion and to be manually removable from the reservoir container retaining portion once received by the reservoir container retaining portion;
a lead shaft supported and carried for rotation about a lead shaft axis by the second housing, the lead shaft having a threaded portion located external to the enclosed interior volume of the second housing, the threaded portion of the lead shaft being arranged to engage the piston plunger at an engagement location on the piston plunger and move the piston plunger along the axis of the reservoir with rotation of the lead shaft when the second housing is engaged with the first housing, the lead shaft axis being laterally offset from the axis of the reservoir at the engagement location, the lead shaft having a connection portion located within the enclosed interior volume of the second housing, wherein the lead shaft extends through an aperture in the second housing between the interior volume of the second housing portion and the exterior volume; and
a drive device operatively connected to the connection portion of the lead shaft, to selectively rotate the lead shaft.

30. A device according to claim 29, further comprising a seal adjacent to the aperture in the second housing, to seal the aperture through which the lead shaft extends.

31. A device according to claim 29, further comprising electrical control circuitry contained in the second housing, wherein the electrical control circuitry controls the delivery of infusion medium from the reservoir to the user when the second housing and the first housing are engaged.

32. A device according to claim 29, further comprising first and second supports for supporting the lead shaft for rotation in the second housing, the first and second supports being spaced apart from each other.

33. A device according to claim 32, wherein the first housing has an interior volume and wherein the reservoir container is contained fully within the interior volume of the first housing.

34. A device for conveying a fluidic medium to or from a user, the device comprising:
- a first housing adapted to be carried by a user, the first housing including a reservoir container retaining portion;
- a second housing configured to be selectively engaged with and disengaged from the first housing, the second housing having an enclosure structure that separates an enclosed interior volume from an exterior volume located external to the enclosure structure;
- a reservoir comprising a container having an interior for containing a fluidic medium and a piston plunger moveable within the interior of the reservoir container, wherein the reservoir container is supported and carried by the first housing, the reservoir container being configured to be received by the reservoir container retaining portion and to be manually removable from the reservoir container retaining portion once received by the reservoir container retaining portion;
- a lead shaft supported and carried for rotation by the second housing, the lead shaft having a threaded portion located external to the enclosed interior volume of the second housing for engaging the piston plunger and moving the piston plunger with rotation of the lead shaft when the second housing is engaged with the first housing, the lead shaft having a connection portion located within the enclosed interior volume of the second housing, wherein the lead shaft extends through an aperture in the second housing between the interior volume of the second housing portion and the exterior volume;
- a drive device operatively connected to the connection portion of the lead shaft, to selectively rotate the lead shaft; and
- first and second supports for supporting the lead shaft for rotation in the second housing, the first and second supports being spaced apart from each other;
- wherein the threaded portion of the lead shaft external to the enclosed interior volume of the second housing for engaging the piston plunger is located between the first and second supports.

* * * * *